(12) United States Patent
Bériault et al.

(10) Patent No.: US 10,835,761 B2
(45) Date of Patent: Nov. 17, 2020

(54) REAL-TIME PATIENT MOTION MONITORING USING A MAGNETIC RESONANCE LINEAR ACCELERATOR (MR-LINAC)

(71) Applicant: Elekta, Inc., Atlanta, GA (US)

(72) Inventors: Silvain Bériault, Longueuil (CA); Martin Emile Lachaine, Montreal (CA)

(73) Assignee: Elekta, Inc., Atlanta, GA (US)

( * ) Notice: Subject to any disclaimer, the term of this patent is extended or adjusted under 35 U.S.C. 154(b) by 0 days.

(21) Appl. No.: 16/170,818

(22) Filed: Oct. 25, 2018

(65) Prior Publication Data

US 2020/0129784 A1    Apr. 30, 2020

(51) Int. Cl.
*A61K 49/06*     (2006.01)
*A61N 5/10*      (2006.01)
(Continued)

(52) U.S. Cl.
CPC ......... *A61N 5/1048* (2013.01); *A61N 5/1037* (2013.01); *G06N 3/08* (2013.01); *G06N 7/08* (2013.01); *G06T 7/0014* (2013.01); *G06T 7/30* (2017.01); *G06T 2207/10076* (2013.01); *G06T 2207/10081* (2013.01); *G06T 2207/10088* (2013.01); *G06T 2207/10104* (2013.01);
(Continued)

(58) Field of Classification Search
CPC .... G01T 1/16; G01T 1/17; G01T 7/00; H04N 5/32
See application file for complete search history.

(56) References Cited

U.S. PATENT DOCUMENTS 9,495,746 B2    11/2016    Chou et al.
9,764,162 B1 *   9/2017    Willcut .................. G16H 50/30
(Continued)

FOREIGN PATENT DOCUMENTS

WO    WO-2011133606 A3    12/2011
WO    WO-2020086976 A1     4/2020
WO    WO-2020086982 A1     4/2020

OTHER PUBLICATIONS

Chou, Chen-Rui, et al., "A learning-based patient repositioning method from limited-angle projections", (2010), 12 pgs.
(Continued)

*Primary Examiner* — David P Porta
*Assistant Examiner* — Mamadou Faye
(74) *Attorney, Agent, or Firm* — Schwegman Lundberg & Woessner, P.A.; Sanjay Agrawal

(57) ABSTRACT

Systems and techniques may be used to estimate a real-time patient state during a radiotherapy treatment using a magnetic resonance linear accelerator (MR-Linac). For example, a method may include generating a dictionary of expanded potential patient measurements and corresponding potential patient states using a preliminary motion model. The method may include training, using a machine learning technique, a correspondence motion model relating an input patient measurement to an output patient state using the dictionary. The method may include estimating, using a processor, the patient state corresponding to a 2D MR image using the correspondence motion model. The method may include directing radiation therapy, using the MR-Linac, to a target according to the patient state.

20 Claims, 8 Drawing Sheets

(51) Int. Cl.
*G06T 7/30* (2017.01)
*G06N 3/08* (2006.01)
*G06N 7/08* (2006.01)
*G06T 7/00* (2017.01)

(52) U.S. Cl.
CPC ............... *G06T 2207/10132* (2013.01); *G06T 2207/30096* (2013.01)

(56) References Cited

U.S. PATENT DOCUMENTS

| | | | |
|---|---|---|---|
| 2014/0107390 A1 | 4/2014 | Brown et al. | |
| 2014/0213904 A1 | 7/2014 | Chen et al. | |
| 2016/0012592 A1 | 1/2016 | Chou et al. | |
| 2017/0360325 A1* | 12/2017 | Hebert | G01R 33/4808 |
| 2019/0154785 A1* | 5/2019 | Zhou | G01R 33/56325 |
| 2019/0287682 A1* | 9/2019 | van Zon | G16H 50/30 |
| 2020/0129780 A1 | 4/2020 | Lachaine et al. | |

OTHER PUBLICATIONS

Chou, Chen-Rui, et al., "CLARET: A Fast Deformable Registration Method Applied to Lung Radiation Therapy", Fourth International (MICCAI) Workshop on Pulmonary Image Analysis, (2011), 113-124.

Jacobs, F, et al., "A Fast Algorithm to Calculate the Exact Radiological Path Through a Pixel or Voxel Space", J Comput. Inf. Technol. vol. 6, (1998).

Li, R, et al., "3D tumor localization through real-time volumetric x-ray imaging for lung cancer radiotherapy", Medical Physics, 38(5), (2011), 2783-2794.

Siddon, R L, "Fast calculation of the exact radiological path for a three-dimensional CT array", Med Phys vol. 12 No. 2, (Mar. 1985), 5 pgs.

Weinberger, Kilian Q, et al., "Metric Learning for Kernel Regression", Journal of Machine Learning Research, (2007), 8 pgs.

Xu, Y, et al., "A method for volumetric imaging in radiotherapy using single x-ray projection", Med Phys vol. 42 No. 5, (May 2015), 2498-2509.

"U.S. Appl. No. 16/170,807, Restriction Requirement dated May 14, 2020", 7 pgs.

"International Application Serial No. PCT/US2019/058090, International Search Report dated Mar. 27, 2020", 7 pgs.

"International Application Serial No. PCT/US2019/058090, Invitation to Pay Additional Fees dated Feb. 6, 2020", 16 pgs.

"International Application Serial No. PCT/US2019/058090, Written Opinion dated Mar. 27, 2020", 13 pgs.

"International Application Serial No. PCT/US2019/058105, International Search Report dated Feb. 4, 2020", 5 pgs.

"International Application Serial No. PCT/US2019/058105, Written Opinion dated Feb. 4, 2020", 11 pgs.

Bjorn, Stemkens, et al., "Image-driven, modei-based 3D abdominal motion estimation for MR-guided radiotherapy", Physics in Medicine and Biology, Institute of Physics Publishing, Bristol GB, vol. 61, No. 14, (Jun. 30, 2016), 21 pgs.

Chetvertkov, Mikhail A, et al., "Use of regularized principal component analysis to model anatomical changes during head and neck radiation therapy for treatment adaptation and response assessment", Medical Physics, Aip, Melville, NY, US, vol. 43, No. 10, (Sep. 6, 2016), XP012211772, ISSN: 0094-2405, DOI: 10.1118/1.4961746, [retrieved on Sep. 6, 2016], (Sep. 6, 2016), 5307-5319.

Kontaxis, C, et al., "Towards fast onhne mtrafractson replanning for free-breathing stereotactic body radiation therapy with the MR-iinac", Physics in Medicine and Biology, Institute of Physics Publishing, Bristol GB, vol. 62, No. 18,, (Aug. 21, 2017), 16 pgs.

Kontaxis, C, et al., "Towards fast online intrafraction replanning for free-breathing stereotactic body radiation therapy with the MR-linac", Physics in Medicine and Biology, Institute of Physics Publishing, Bristol GB, vol. 62, No. 18, XP020319605, ISSN: 0031-9155, DOI: 10.1088/1361-6560/AA82AE, [retrieved on Aug. 21, 2017], (Aug. 21, 2017), 7233-7248.

Li, Ruijiang, et al., "Real-time volumetric image reconstruction and 3D tumor localization based on a single x-ray projection image for lung cancer radiotherapy", Medical Physics, Aip, Melville, NY, US, vol. 37, No. 6, XP012135815, (May 21, 2010), 2822-2826.

Stemkens, Bjorn, et al., "Image-driven, model-based 3D abdominal motion estimation for MR-guided radiotherapy", Physics in Medicine and Biology, Institute of Physics Publishing, Bristol GB, vol. 61, No. 14, XP020306611, [retrieved on Jun. 30, 2016], (Jun. 30, 2016), 5335-5355.

Wei, Ran, et al., "A CNN based volumetric imaging method with single X-ray projection", 2017 IEEE International Conference on Imaging Systems and Techniques (1ST), IEEE, XP033302050, DOI: 10.1109/IST.2017.8261550, [retrieved on Jan. 16, 2018], (Oct. 18, 2017), 1-6.

* cited by examiner

REAL-TIME PATIENT MOTION MONITORING USING A MAGNETIC RESONANCE LINEAR ACCELERATOR (MR-LINAC)

TECHNICAL FIELD

Embodiments of the present disclosure pertain generally to medical image and artificial intelligence processing techniques. In particular, the present disclosure pertains to use of machine learning for real-time patient state estimation.

BACKGROUND

In radiotherapy or radiosurgery, treatment planning is typically performed based on medical images of a patient and requires the delineation of target volumes and normal critical organs in the medical images. One challenge occurs with accurately tracking the various objects, such as a tumor, healthy tissue, or other aspects of patient anatomy when the patient is moving (e.g., breathing).

Current techniques are unable to directly measure a changing patient state in real-time. For example, some techniques use 2D imaging, such as 2D kV projections or 2D MRI slices, which are not able to completely track the various objects.

Other techniques may rely on detecting surface information, either directly or by tracking markers on a vest or a box affixed to the patient. These techniques assume that the surface information is correlated to internal patient state, which is often not accurate.

Yet other techniques may rely on implanting markers, such as magnetically tracked markers, or using x-ray detection of radio-opaque markers. These techniques are invasive and correspond only to limited points within the patient.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

Figure 1:
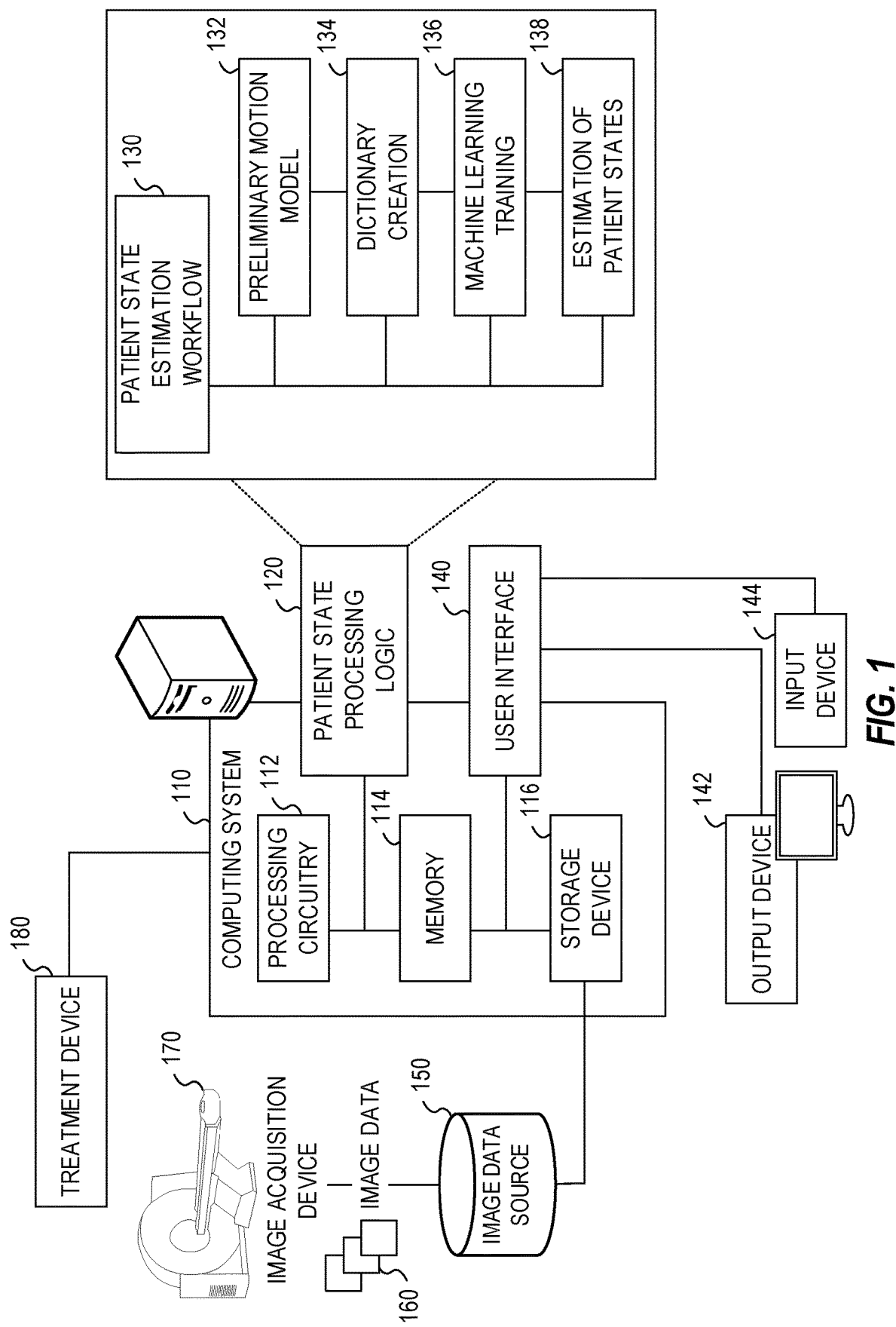
FIG. 1 illustrates an exemplary radiotherapy system adapted for performing image patient state estimation processing.

In the following detailed description, reference is made to the accompanying drawings which form a part hereof, and which is shown by way of illustration-specific embodiments in which the present invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not be taken in a limiting sense, and the scope of the present invention is defined by the appended claims and their equivalents.

Image guided radiation therapy (IGRT) is a technique that makes use of imaging of a patient, in treatment position, immediately prior to irradiation. This allows more accurate targeting of anatomy, such as an organs, tumors or organs-at-risk. If the patient is expected to move during treatment, for example motion caused by breathing which creates a quasi-periodic motion of a lung tumor, or bladder filling causing the prostate position to drift, additional margins may be placed around the target to encompass the expected patient motion. These larger margins come at the expense of high dose to surrounding normal tissue, which may lead to increased side-effects.

IGRT may use computed tomography (CT) imaging, cone beam CT (CBCT), magnetic resonance (MR) imaging, positron-emission tomography (PET) imaging, or the like to obtain a 3D or 4D image of a patient prior to irradiation. For example, a CBCT-enabled linac (linear accelerator) may consist of a kV source/detector affixed to the gantry at a 90 degree angle to a radiation beam, or a MR-Linac device may consist of a linac integrated directly with an MR scanner.

Localizing motion during the actual irradiation treatment delivery (intrafraction motion) may allow reduction of additional treatment margins that would otherwise be used to encompass motion, thus either allowing higher doses to be delivered, reduction of side-effects, or both. Many IGRT imaging technologies are generally not sufficiently fast for imaging intrafractional motion. For example, CBCT requires multiple kV images from various angles to reconstruct a full 3D patient image, and a 3D MR requires multiple 2D slices, or filling of the full 3D k-space, each of which may take minutes to generate a full 3D image.

In some cases, the real-time or quasi-real-time data that would usually be completely acquired prior to generation of a 3D IGRT image, can be used as it is gathered to estimate the instantaneous 3D image at a much faster refresh rate from the incomplete, yet fast, stream of incoming information. For example, 2D kV projections or 2D MR slices may be used to estimate a full 3D CBCT-like or 3D MR-like image that evolves with the actual patient motion during treatment. Although fast, on their own these 2D images provide only a particular perspective of the patient, not the full 3D picture.

A patient state generator may receive partial measurements (e.g., a 2D image) as an input and generate (e.g., estimate) a patient state (e.g., a 3D image) as an output. To generate a patient state, the generator may use a single current partial measurement, a future (predicted) or past partial measurement, or a number of partial measurements (e.g., the last 10 measurements). These partial measurements may be from a single modality, such as an x-ray projection or MRI slice, or from multiple modalities, such as positions of reflective surface markers on the patient's surface synchronized with x-ray projections. A patient state may be a 3D image, or of 'multi-modality,' for example the patient state may include two or more 3D images that offer different information on the patient state, such as a 'MR-like' for enhanced tissue contrast, a 'CT-like' for high geometric accuracy and voxels related to density that are useful for dose calculations, or a 'functional MR-like' to provide function information about the patient. Patient state may also include non-imaging information. A patient state include one or more points of interest (such as a target position), contours, surfaces, deformation vector fields, or any information that is relevant to optimizing patient treatments.

Partial measurements described above may be received in a real-time stream of images (e.g., 2D images) taken from a kV imager or a MR imager, for example. The kV imager may produce stereoscopic 2D images for the real-time stream (e.g., two x-ray images that are orthogonal and acquired substantially simultaneously). The kV imager may be fixed in a room or coupled to a treatment device (e.g., attached to a gantry). The MR imager may produce 2D MR slices, which may be orthogonal or parallel. A patient state may be generated from an image or pair of images received. For example, at any given moment in time, the patient state for the last received image from the real-time stream may be generated.

In an example, a patient model may be based on data currently collected in a given fraction, in a pre-treatment phase (after the patient is set up and before the beam is turned on), from another fraction or during simulation/planning, using other patients, using generalized patient anatomy, using mechanical models, or any other information that may assist in defining a patient state from partial measurements. In an example, the patient model is a 4D dataset, acquired pre-treatment, which represents changes in patient state over a limited period of time (e.g. one representative respiratory cycle). The patient model may be trained, (e.g., using a machine learning technique), to relate an input patient measurement (e.g., an image or pair of images from a real-time stream) to an output patient state, for example using a dictionary defining constructed patient measurements to corresponding patient states. The patient model may be warped by a deformation vector field (DVF) as a function of one or more parameters to generate a patient state.

The patient model in a 4D dataset may include the patient state that varies with a single parameter, such as phase in a respiratory cycle. The patient model may be used to build a time-varying patient state over a representative breathing cycle, which may treat each breath as more or less the same. This simplifies the modeling by allowing chunks of partial imaging data to be taken from different breathing cycles and assigned to a single representative breathing cycle. A 3D image may then be reconstructed for each phase 'bin'.

In an example, the patient state may be represented, for example, as a 3D image, or a 3D DVF plus a 3D reference image. These may be equivalent, since the elements of the 3D DVF and the 3D reference image may be used to obtain (e.g., deform the 3D reference image with the 3D DVF) the 3D image.

FIG. 1 illustrates an exemplary radiotherapy system adapted for performing patient state estimation processing. This patient state estimation processing is performed to enable the radiotherapy system to provide radiation therapy to a patient based on specific aspects of captured medical imaging data. The radiotherapy system includes an image processing computing system 110 which hosts patient state processing logic 120. The image processing computing system 110 may be connected to a network (not shown), and such network may be connected to the Internet. For instance, a network can connect the image processing computing system 110 with one or more medical information sources (e.g., a radiology information system (RIS), a medical record system (e.g., an electronic medical record (EMR)/electronic health record (EHR) system), an oncology information system (OIS)), one or more image data sources 150, an image acquisition device 170, and a treatment device 180 (e.g., a radiation therapy device). As an example, the image processing computing system 110 can be configured to perform image patient state operations by executing instructions or data from the patient state processing logic 120, as part of operations to generate and customize radiation therapy treatment plans to be used by the treatment device 180.

The image processing computing system 110 may include processing circuitry 112, memory 114, a storage device 116, and other hardware and software-operable features such as a user interface 140, communication interface, and the like. The storage device 116 may store computer-executable instructions, such as an operating system, radiation therapy treatment plans (e.g., original treatment plans, adapted treatment plans, or the like), software programs (e.g., radiotherapy treatment plan software, artificial intelligence implementations such as deep learning models, machine learning models, and neural networks, etc.), and any other computer-executable instructions to be executed by the processing circuitry 112.

In an example, the processing circuitry 112 may include a processing device, such as one or more general-purpose processing devices such as a microprocessor, a central processing unit (CPU), a graphics processing unit (GPU), an accelerated processing unit (APU), or the like. More particularly, the processing circuitry 112 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processing circuitry 112 may also be implemented by one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some examples, the processing circuitry 112 may be a special-purpose processor, rather than a general-purpose processor. The processing circuitry 112 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processing circuitry 112 may also include graphical processing units such as a GPU from the GeForce®, Quadro®, Tesla® family manufactured by Nvidia™, GMA, Iris™ family manufactured by Intel™, or the Radeon™ family manufactured by AMD™. The processing circuitry 112 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor, for example, a multi-core design or a plurality of processors each having a multi-core design. The processing circuitry 112 can execute sequences of computer program instructions, stored in memory 114, and accessed from the storage device 116, to perform various operations, processes, methods that will be explained in greater detail below.

The memory 114 may comprise read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including image, data, or computer executable instructions (e.g., stored in any format) capable of being accessed by the processing circuitry 112, or any other type of computer device. For instance, the computer program instructions can be accessed by the processing circuitry 112, read from the ROM, or any other suitable memory location, and loaded into the RAM for execution by the processing circuitry 112.

The storage device 116 may constitute a drive unit that includes a machine-readable medium on which is stored one or more sets of instructions and data structures (e.g., software) embodying or utilized by any one or more of the methodologies or functions described herein (including, in various examples, the patient state processing logic 120 and the user interface 140). The instructions may also reside, completely or at least partially, within the memory 114 and/or within the processing circuitry 112 during execution thereof by the image processing computing system 110, with the memory 114 and the processing circuitry 112 also constituting machine-readable media.

The memory device 114 or the storage device 116 may constitute a non-transitory computer-readable medium. For example, the memory device 114 or the storage device 116 may store or load instructions for one or more software applications on the computer-readable medium. Software applications stored or loaded with the memory device 114 or the storage device 116 may include, for example, an operating system for common computer systems as well as for software-controlled devices. The image processing computing system 110 may also operate a variety of software programs comprising software code for implementing the patient state processing logic 120 and the user interface 140. Further, the memory device 114 and the storage device 116 may store or load an entire software application, part of a software application, or code or data that is associated with a software application, which is executable by the processing circuitry 112. In a further example, the memory device 114 or the storage device 116 may store, load, or manipulate one or more radiation therapy treatment plans, imaging data, patient state data, dictionary entries, artificial intelligence model data, labels and mapping data, etc. It is contemplated that software programs may be stored not only on the storage device 116 and the memory 114 but also on a removable computer medium, such as a hard drive, a computer disk, a CD-ROM, a DVD, a HD, a Blu-Ray DVD, USB flash drive, a SD card, a memory stick, or any other suitable medium; such software programs may also be communicated or received over a network.

Although not depicted, the image processing computing system 110 may include a communication interface, network interface card, and communications circuitry. An example communication interface may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a IEEE 802.11/Wi-Fi adapter), a telecommunication adapter (e.g., to communicate with 3G, 4G/LTE, and 5G, networks and the like), and the like. Such a communication interface may include one or more digital and/or analog communication devices that permit a machine to communicate with other machines and devices, such as remotely located components, via a network. The network may provide the functionality of a local area network (LAN), a wireless network, a cloud computing environment (e.g., software as a service, platform as a service, infrastructure as a service, etc.), a client-server, a wide area network (WAN), and the like. For example, network may be a LAN or a WAN that may include other systems (including additional image processing computing systems or image-based components associated with medical imaging or radiotherapy operations).

In an example, the image processing computing system 110 may obtain image data 160 from the image data source 150, for hosting on the storage device 116 and the memory 114. In an example, the software programs operating on the image processing computing system 110 may convert medical images of one format (e.g., MRI) to another format (e.g., CT), such as by producing synthetic images, such as a pseudo-CT image. In another example, the software programs may register or associate a patient medical image (e.g., a CT image or an MR image) with that patient's dose distribution of radiotherapy treatment (e.g., also represented as an image) so that corresponding image voxels and dose voxels are appropriately associated. In yet another example, the software programs may substitute functions of the patient images such as signed distance functions or processed versions of the images that emphasize some aspect of the image information. Such functions might emphasize edges or differences in voxel textures, or other structural aspects. In another example, the software programs may visualize, hide, emphasize, or de-emphasize some aspect of anatomical features, patient measurements, patient state information, or dose or treatment information, within medical images. The storage device 116 and memory 114 may store and host data to perform these purposes, including the image data 160, patient data, and other data required to create and implement a radiation therapy treatment plan and associated patient state estimation operations.

The processing circuitry 112 may be communicatively coupled to the memory 114 and the storage device 116, and the processing circuitry 112 may be configured to execute computer executable instructions stored thereon from either the memory 114 or the storage device 116. The processing circuitry 112 may execute instructions to cause medical images from the image data 160 to be received or obtained in memory 114, and processed using the patient state processing logic 120. For example, the image processing computing system 110 may receive image data 160 from the image acquisition device 170 or image data sources 150 via a communication interface and network to be stored or cached in the storage device 116. The processing circuitry 112 may also send or update medical images stored in memory 114 or the storage device 116 via a communication interface to another database or data store (e.g., a medical facility database). In some examples, one or more of the systems may form a distributed computing/simulation environment that uses a network to collaboratively perform the embodiments described herein. In addition, such network may be connected to internet to communicate with servers and clients that reside remotely on the internet.

In further examples, the processing circuitry 112 may utilize software programs (e.g., a treatment planning software) along with the image data 160 and other patient data to create a radiation therapy treatment plan. In an example, the image data 160 may include 2D or 3D images, such as from a CT or MR. In addition, the processing circuitry 112 may utilize software programs to generate an estimated patient state from a dictionary of measurements and corresponding patient states, such as using a correspondence motion model and a machine learning algorithm (e.g., a regression algorithm).

Further, such software programs may utilize patient state processing logic 120 to implement a patient state estimation workflow 130, using the techniques further discussed herein. The processing circuitry 112 may subsequently then transmit the executable radiation therapy treatment plan via a communication interface and the network to the treatment device 180, where the radiation therapy plan will be used to treat a patient with radiation via the treatment device, consistent with results of the patient state estimation workflow 130. Other outputs and uses of the software programs and the patient state estimation workflow 130 may occur with use of the image processing computing system 110.

As discussed herein (e.g., with reference to the patient state estimation discussed herein, the processing circuitry 112 may execute software programs that invokes the patient state processing logic 120 to implement functions including generation of a preliminary motion model, creation of a dictionary, training a patient state generator using machine learning, patient state estimation, and other aspects of automatic processing and artificial intelligence. For instance, the processing circuitry 112 may execute software programs that estimate a patient state using a machine learning trained system.

In an example, the image data 160 may include one or more MRI images (e.g., 2D MRI, 3D MRI, 2D streaming MRI, 4D MRI, 4D volumetric MRI, 4D cine MRI, etc.), functional MRI images (e.g., fMRI, DCE-MRI, diffusion MRI), Computed Tomography (CT) images (e.g., 2D CT, Cone beam CT, 3D CT, 4D CT), ultrasound images (e.g., 2D ultrasound, 3D ultrasound, 4D ultrasound), Positron Emission Tomography (PET) images, X-ray images, fluoroscopic images, radiotherapy portal images, Single-Photo Emission Computed Tomography (SPECT) images, computer generated synthetic images (e.g., pseudo-CT images) and the like. Further, the image data 160 may also include or be associated with medical image processing data, for instance, training images, and ground truth images, contoured images, and dose images. In an example, the image data 160 may be received from the image acquisition device 170 and stored in one or more of the image data sources 150 (e.g., a Picture Archiving and Communication System (PACS), a Vendor Neutral Archive (VNA), a medical record or information system, a data warehouse, etc.). Accordingly, the image acquisition device 170 may comprise a MRI imaging device, a CT imaging device, a PET imaging device, an ultrasound imaging device, a fluoroscopic device, a SPECT imaging device, an integrated Linear Accelerator and MRI imaging device, or other medical imaging devices for obtaining the medical images of the patient. The image data 160 may be received and stored in any type of data or any type of format (e.g., in a Digital Imaging and Communications in Medicine (DICOM) format) that the image acquisition device 170 and the image processing computing system 110 may use to perform operations consistent with the disclosed embodiments.

In an example, the image acquisition device 170 may be integrated with the treatment device 180 as a single apparatus (e.g., a MRI device combined with a linear accelerator, also referred to as an "MR-linac", as shown and described in FIG. 3 below). Such an MR-linac can be used, for example, to precisely determine a location of a target organ or a target tumor in the patient, so as to direct radiation therapy accurately according to the radiation therapy treatment plan to a predetermined target. For instance, a radiation therapy treatment plan may provide information about a particular radiation dose to be applied to each patient. The radiation therapy treatment plan may also include other radiotherapy information, such as beam angles, dose-histogram-volume information, the number of radiation beams to be used during therapy, the dose per beam, and the like.

The image processing computing system 110 may communicate with an external database through a network to send/receive a plurality of various types of data related to image processing and radiotherapy operations. For example, an external database may include machine data that is information associated with the treatment device 180, the image acquisition device 170, or other machines relevant to radiotherapy or medical procedures. Machine data information may include radiation beam size, arc placement, beam on and off time duration, machine parameters, segments, multi-leaf collimator (MLC) configuration, gantry speed, MRI pulse sequence, and the like. The external database may be a storage device and may be equipped with appropriate database administration software programs. Further, such databases or data sources may include a plurality of devices or systems located either in a central or a distributed manner.

The image processing computing system 110 can collect and obtain data, and communicate with other systems, via a network using one or more communication interfaces, which are communicatively coupled to the processing circuitry 112 and the memory 114. For instance, a communication interface may provide communication connections between the image processing computing system 110 and radiotherapy system components (e.g., permitting the exchange of data with external devices). For instance, the communication interface may in some examples have appropriate interfacing circuitry from an output device 142 or an input device 144 to connect to the user interface 140, which may be a hardware keyboard, a keypad, or a touch screen through which a user may input information into the radiotherapy system.

As an example, the output device 142 may include a display device which outputs a representation of the user interface 140 and one or more aspects, visualizations, or representations of the medical images. The output device 142 may include one or more display screens that display medical images, interface information, treatment planning parameters (e.g., contours, dosages, beam angles, labels, maps, etc.) treatment plans, a target, localizing a target or tracking a target, patient state estimations (e.g., a 3D image), or any related information to the user. The input device 144 connected to the user interface 140 may be a keyboard, a keypad, a touch screen or any type of device that a user may input information to the radiotherapy system. Alternatively, the output device 142, the input device 144, and features of the user interface 140 may be integrated into a single device such as a smartphone or tablet computer, e.g., Apple iPad®, Lenovo Thinkpad®, Samsung Galaxy®, etc.

Furthermore, any and all components of the radiotherapy system may be implemented as a virtual machine (e.g., via VMWare, Hyper-V, and the like virtualization platforms). For instance, a virtual machine can be software that functions as hardware. Therefore, a virtual machine can include at least one or more virtual processors, one or more virtual memories, and one or more virtual communication interfaces that together function as hardware. For example, the image processing computing system 110, the image data sources 150, or like components, may be implemented as a virtual machine or within a cloud-based virtualization environment.

The patient state processing logic 120 or other software programs may cause the computing system to communicate with the image data sources 150 to read images into memory 114 and the storage device 116, or store images or associated data from the memory 114 or the storage device 116 to and from the image data sources 150. For example, the image data source 150 may be configured to store and provide a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DICOM) metadata, etc.) that the image data source 150 hosts, from image sets in image data 160 obtained from one or more patients via the image acquisition device 170. The image data source 150 or other databases may also store data to be used by the patient state processing logic 120 when executing a software program that performs patient state estimation operations, or when creating radiation therapy treatment plans. Further, various databases may store the data produced by the preliminary motion model (such as the dictionary), the correspondence motion model, or machine learning models, including the network parameters constituting the model learned by the network and the resulting predicted data. The image processing computing system 110 thus may obtain and/or receive the image data 160 (e.g., 2D MRI slice images, CT images, 2D Fluoroscopy images, X-ray images, 3D MRI images, 4D MRI images, etc.) from the image data source 150, the image acquisition device 170, the treatment device 180 (e.g., a MRI-Linac), or other information systems, in connection with performing image patient state estimation as part of treatment or diagnostic operations.

The image acquisition device 170 can be configured to acquire one or more images of the patient's anatomy for a region of interest (e.g., a target organ, a target tumor or both). Each image, typically a 2D image or slice, can include one or more parameters (e.g., a 2D slice thickness, an orientation, and a location, etc.). In an example, the image acquisition device 170 can acquire a 2D slice in any orientation. For example, an orientation of the 2D slice can include a sagittal orientation, a coronal orientation, or an axial orientation. The processing circuitry 112 can adjust one or more parameters, such as the thickness and/or orientation of the 2D slice, to include the target organ and/or target tumor. In an example, 2D slices can be determined from information such as a 3D MRI volume. Such 2D slices can be acquired by the image acquisition device 170 in "real-time" while a patient is undergoing radiation therapy treatment, for example, when using the treatment device 180 (with "real-time" meaning acquiring the data in 10 milliseconds or less). In another example for some applications, real-time may include a timeframe within (e.g., up to) 200 or 300 milliseconds. In an example, real-time may include a time period fast enough for a clinical problem being solved by techniques described herein. In this example, real-time may vary depending on target speed, radiotherapy margins, lag, response time of a treatment device, etc.

The patient state processing logic 120 in the image processing computing system 110 is depicted as implementing a patient state estimation workflow 130 with various aspects of model generation and estimation processing operations. In an example, the patient state estimation workflow 130 operated by the patient state processing logic 120 generates and uses a preliminary motion model 132 generated from patient data (e.g., from a patient being treated, from multiple previous patients, or the like). The preliminary motion model 132 may include a model of a patient under motion (e.g., breathing) generated based on patient measurements and corresponding patient states. The patient state estimation workflow 130 includes creation of a dictionary 134 by using the preliminary motion model to generate sample (potential) patient measurements and corresponding patient states. The patient state estimation workflow 130 includes training a correspondence motion model using machine learning 136 (e.g., using a regression-based machine learning technique) based on the dictionary 134. The patient state estimation workflow 130 includes estimating a patient state 138 using the correspondence motion model and a current patient measurement (e.g., 2D image).

The patient state processing logic 120 and the patient state estimation workflow 130 may be used when generating the radiation therapy treatment plan, within use of software programs such as treatment planning software, such as Monaco®, manufactured by Elekta AB of Stockholm, Sweden. In order to generate the radiation therapy treatment plans, the image processing computing system 110 may communicate with the image acquisition device 170 (e.g., a CT device, a MRI device, a PET device, an X-ray device, an ultrasound device, etc.) to capture and access images of the patient and to delineate a target, such as a tumor. In some examples, the delineation of one or more organs at risk (OARs), such as healthy tissue surrounding the tumor or in close proximity to the tumor may be required.

In order to delineate a target organ or a target tumor from the OAR, medical images, such as MRI images, CT images, PET images, fMRI images, X-ray images, ultrasound images, radiotherapy portal images, SPECT images and the like, of the patient undergoing radiotherapy may be obtained non-invasively by the image acquisition device 170 to reveal the internal structure of a body part. Based on the information from the medical images, a 3D structure of the relevant anatomical portion may be obtained. In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible), for example by using an estimated patient state to determine where OAR(s) may be at a given time when the patient is moving (e.g., breathing). Other parameters that may be considered include the location of the target organ and the target tumor, the location of the OAR, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker using a program such as Monaco® manufactured by Elekta AB of Stockholm, Sweden) or automatically (e.g., using a program such as the Atlas-based auto-segmentation software, ABAS®, manufactured by Elekta AB of Stockholm, Sweden).

After the target tumor and the OAR(s) have been located and delineated, a dosimetrist, physician or healthcare worker may determine a dose of radiation to be applied to the target tumor, as well as any maximum amounts of dose that may be received by the OAR proximate to the tumor (e.g., left and right parotid, optic nerves, eyes, lens, inner ears, spinal cord, brain stem, and the like). After the radiation dose is determined for each anatomical structure (e.g., target tumor, OAR), a process known as inverse planning may be performed to determine one or more treatment plan parameters that would achieve the desired radiation dose distribution. Examples of treatment plan parameters include volume delineation parameters (e.g., which define target volumes, contour sensitive structures, etc.), margins around the target tumor and OARs, beam angle selection, collimator settings, and beam-on times. During the inverse-planning process, the physician may define dose constraint parameters that set bounds on how much radiation an OAR may receive (e.g., defining full dose to the tumor target and zero dose to any OAR; defining 95% of dose to the target tumor; defining that the spinal cord, brain stem, and optic structures receive ≤45Gy, ≤55Gy and <54Gy, respectively). The result of inverse planning may constitute a radiation therapy treatment plan that may be stored. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, the image processing computing system 110 can generate a tailored radiation therapy treatment plan having these parameters in order for the treatment device 180 to provide suitable radiotherapy treatment to the patient.

Figure 2:
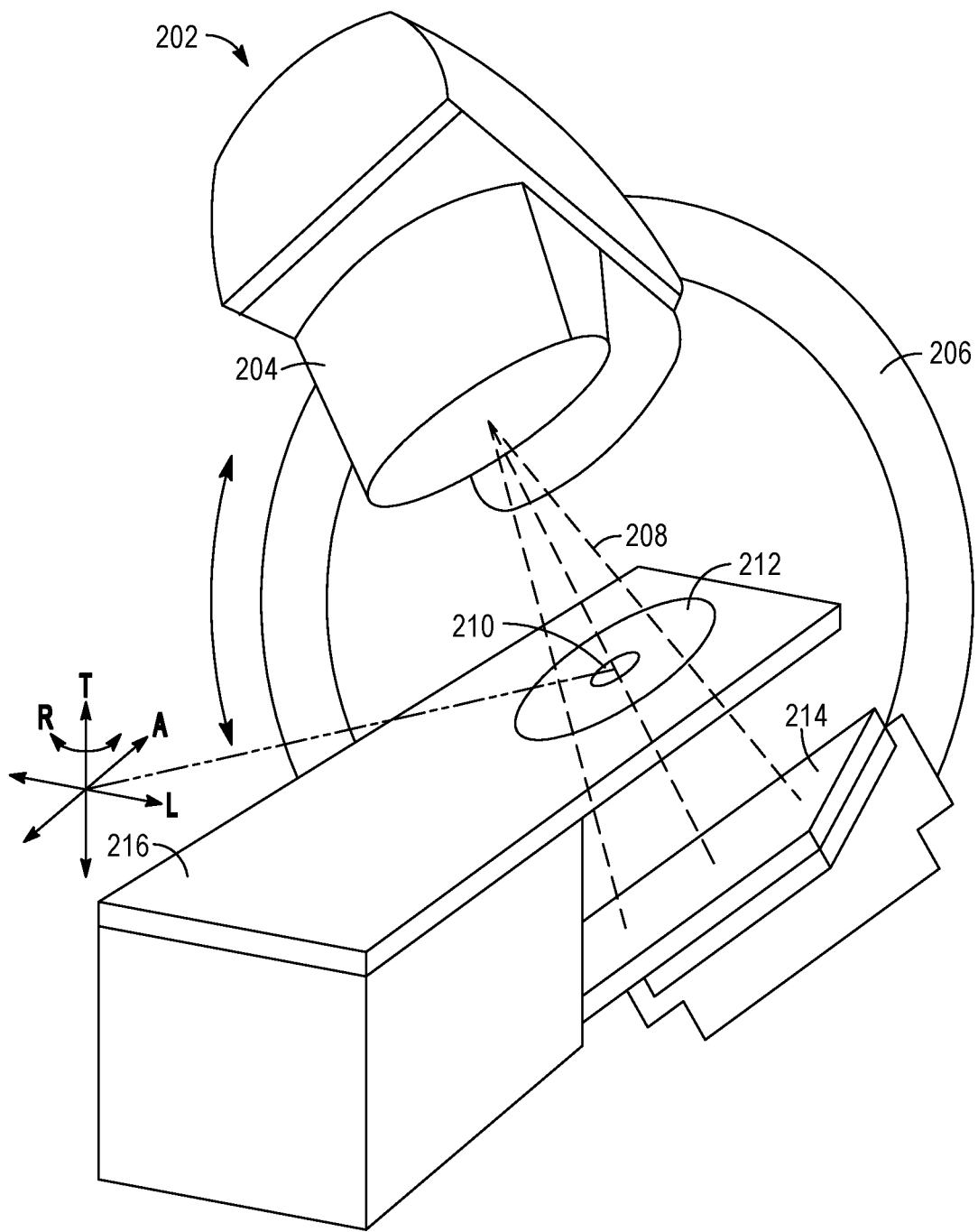
FIG. 2 illustrates an exemplary image-guided radiotherapy device.

FIG. 2 illustrates an exemplary image-guided radiotherapy device 202, that includes include a radiation source, such as an X-ray source or a linear accelerator, a couch 216, an imaging detector 214, and a radiation therapy output 204. The radiation therapy device 202 may be configured to emit a radiation beam 208 to provide therapy to a patient. The radiation therapy output 204 can include one or more attenuators or collimators, such as a multi-leaf collimator (MLC).

As an example, a patient can be positioned in a region 212, supported by the treatment couch 216 to receive a radiation therapy dose according to a radiation therapy treatment plan (e.g., a treatment plan generated by the radiotherapy system of FIG. 1). The radiation therapy output 204 can be mounted or attached to a gantry 206 or other mechanical support. One or more chassis motors (not shown) may rotate the gantry 206 and the radiation therapy output 204 around couch 216 when the couch 216 is inserted into the treatment area. In an example, gantry 206 may be continuously rotatable around couch 216 when the couch 216 is inserted into the treatment area. In another example, gantry 206 may rotate to a predetermined position when the couch 216 is inserted into the treatment area. For example, the gantry 206 can be configured to rotate the therapy output 204 around an axis ("A"). Both the couch 216 and the radiation therapy output 204 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 216 movements or rotations in order to properly position the patient in or out of the radiation beam 208 according to a radiation therapy treatment plan. As both the couch 216 and the gantry 206 are independently moveable from one another in multiple degrees of freedom, which allows the patient to be positioned such that the radiation beam 208 precisely can target the tumor.

The coordinate system (including axes A, T, and L) shown in FIG. 2 can have an origin located at an isocenter 210. The isocenter can be defined as a location where the central axis of the radiation therapy beam 208 intersects the origin of a coordinate axis, such as to deliver a prescribed radiation dose to a location on or within a patient. Alternatively, the isocenter 210 can be defined as a location where the central axis of the radiation therapy beam 208 intersects the patient for various rotational positions of the radiation therapy output 204 as positioned by the gantry 206 around the axis A.

Gantry 206 may also have an attached imaging detector 214. The imaging detector 214 is preferably located opposite to the radiation source (output 204), and in an example, the imaging detector 214 can be located within a field of the therapy beam 208.

The imaging detector 214 can be mounted on the gantry 206 preferably opposite the radiation therapy output 204, such as to maintain alignment with the therapy beam 208. The imaging detector 214 rotating about the rotational axis as the gantry 206 rotates. In an example, the imaging detector 214 can be a flat panel detector (e.g., a direct detector or a scintillator detector). In this manner, the imaging detector 214 can be used to monitor the therapy beam 208 or the imaging detector 214 can be used for imaging the patient's anatomy, such as portal imaging. The control circuitry of radiation therapy device 202 may be integrated within the radiotherapy system or remote from it.

In an illustrative example, one or more of the couch 216, the therapy output 204, or the gantry 206 can be automatically positioned, and the therapy output 204 can establish the therapy beam 208 according to a specified dose for a particular therapy delivery instance. A sequence of therapy deliveries can be specified according to a radiation therapy treatment plan, such as using one or more different orientations or locations of the gantry 206, couch 216, or therapy output 204. The therapy deliveries can occur sequentially, but can intersect in a desired therapy locus on or within the patient, such as at the isocenter 210. A prescribed cumulative dose of radiation therapy can thereby be delivered to the therapy locus while damage to tissue nearby the therapy locus can be reduced or avoided.

Thus, FIG. 2 specifically illustrates an example of a radiation therapy device 202 operable to provide radiotherapy treatment to a patient, with a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a platform supporting the patient can be used to align a radiation therapy isocenter with a specified target locus within the patient. In another example, a radiation therapy device can be a combination of a linear accelerator and an image acquisition device. In some examples, the image acquisition device may be an MRI, an X-ray, a CT, a CBCT, a spiral CT, a PET, a SPECT, an optical tomography, a fluorescence imaging, ultrasound imaging, an MR-linac, or radiotherapy portal imaging device, etc., as would be recognized by one of ordinary skill in the art.

Figure 3:
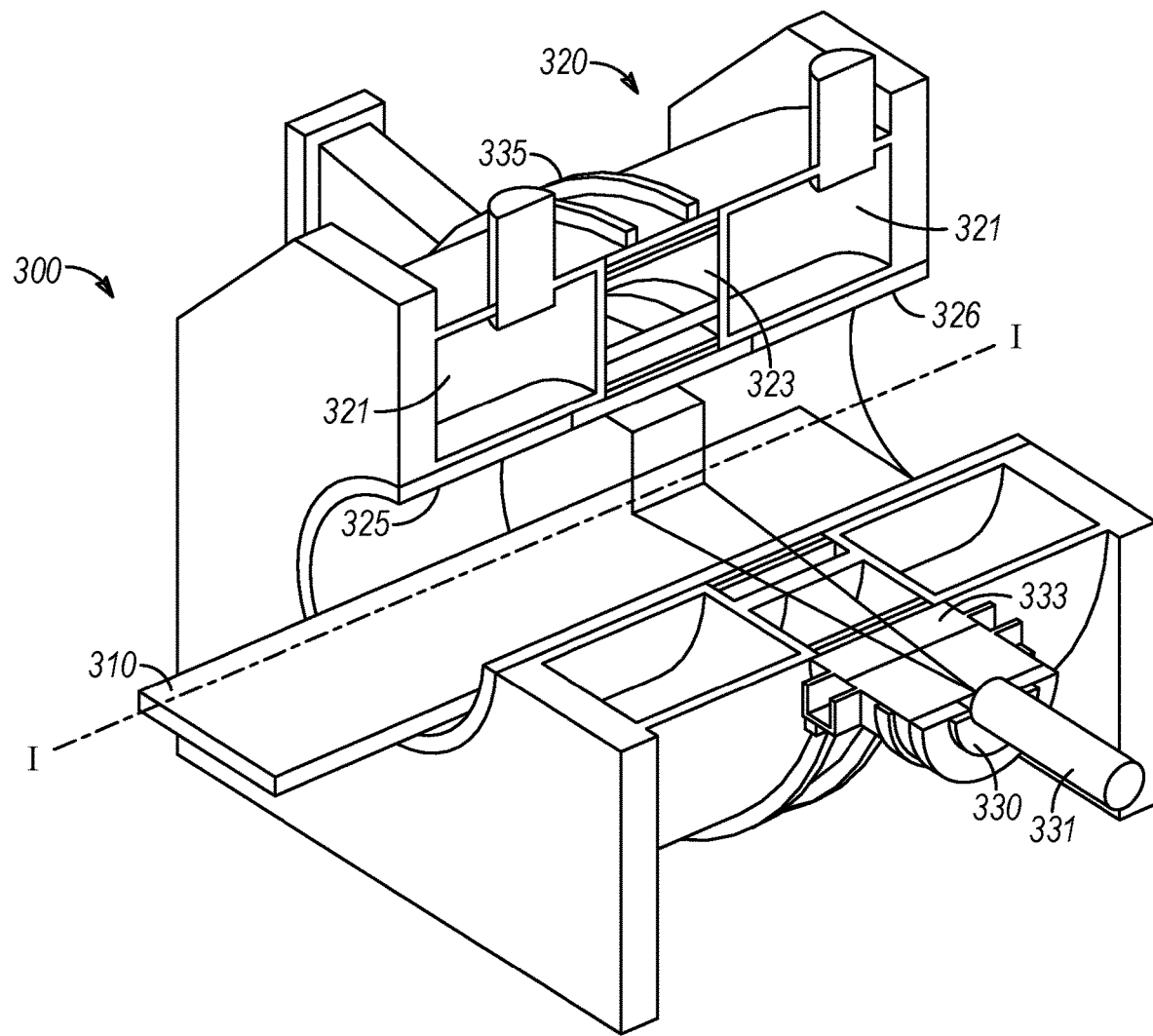
FIG. 3 illustrates a partially cut-away view of an exemplary system including a combined radiation therapy system and an imaging system, such as a nuclear magnetic resonance (MR) imaging system.

FIG. 3 depicts an exemplary radiation therapy system 300 (e.g., known in the art as a MR-Linac) that can include combining a radiation therapy device 202 and an imaging system, such as a nuclear magnetic resonance (MR) imaging system consistent with the disclosed embodiments. As shown, system 300 may include a couch 310, an image acquisition device 320, and a radiation delivery device 330. System 300 delivers radiation therapy to a patient in accordance with a radiotherapy treatment plan. In some embodiments, image acquisition device 320 may correspond to image acquisition device 170 in FIG. 1 that may acquire images.

Couch 310 may support a patient (not shown) during a treatment session. In some implementations, couch 310 may move along a horizontal, translation axis (labelled "I"), such that couch 310 may move the patient resting on couch 310 into or out of system 300. Couch 310 may also rotate around a central vertical axis of rotation, transverse to the translation axis. To allow such movement or rotation, couch 310 may have motors (not shown) enabling the couch to move in various directions and to rotate along various axes. A controller (not shown) may control these movements or rotations in order to properly position the patient according to a treatment plan.

In some embodiments, image acquisition device 320 may include an MRI machine used to acquire 2D or 3D MRI images of the patient before, during, or after a treatment session. Image acquisition device 320 may include a magnet 321 for generating a primary magnetic field for magnetic resonance imaging. The magnetic field lines generated by operation of magnet 321 may run substantially parallel to the central translation axis I. Magnet 321 may include one or more coils with an axis that runs parallel to the translation axis I. In some embodiments, the one or more coils in magnet 321 may be spaced such that a central window 323 of magnet 321 is free of coils. In other embodiments, the coils in magnet 321 may be thin enough or of a reduced density such that they are substantially transparent to radiation of the wavelength generated by radiotherapy device 330. Image acquisition device 320 may also include one or more shielding coils, which may generate a magnetic field outside magnet 321 of approximately equal magnitude and opposite polarity in order to cancel or reduce any magnetic field outside of magnet 321. As described below, radiation source 331 of radiotherapy device 330 may be positioned in the region where the magnetic field is cancelled, at least to a first order, or reduced.

Image acquisition device 320 may also include two gradient coils 325 and 326, which may generate a gradient magnetic field that is superposed on the primary magnetic field. Coils 325 and 326 may generate a gradient in the resultant magnetic field that allows spatial encoding of the protons so that their position can be determined. Gradient coils 325 and 326 may be positioned around a common central axis with the magnet 321, and may be displaced along that central axis. The displacement may create a gap, or window, between coils 325 and 326. In the embodiments where magnet 321 also includes a central window 323 between coils, the two windows may be aligned with each other.

Image acquisition is used to track tumor movement. At times, internal or external surrogates may be used. However, implanted seeds may move from their initial positions or become dislodged during radiation therapy treatment. Also, using surrogates assumes there is a correlation between tumor motion and the displacement of the external surrogate. However, there may be phase shifts between external surrogates and tumor motion, and their positions may frequently lose correlation over time. It is known that there may be mismatches between tumor and surrogates upward of 9 mm. Further, any deformation of the shape of a tumor is unknown during tracking.

An advantage of magnetic resonance imaging (MRI) is in the superior soft tissue contrast that is provided to visualize the tumor in more detail. Using a plurality of intrafractional MR images allows the determination of both shape and position (e.g., centroid) of a tumor. In addition, MRI images improve any manual contouring performed by, for example, a radiation oncologist, even when auto-contouring software (e.g., ABAS®) is utilized. This is because of the high contrast between the tumor target and the background region provided by MR images.

Another advantage of using an MR-Linac system is that a treatment beam can be continuously on and thereby executing intrafractional tracking of the target tumor. For instance, optical tracking devices or stereoscopic x-ray fluoroscopy systems can detect tumor position at 30 Hz by using tumor surrogates. With MRI, the imaging acquisition rates are faster (e.g., 3-6 fps). Therefore, the centroid position of the target may be determined, artificial intelligence (e.g., neural network) software can predict a future target position. An added advantage of intrafractional tracking by using an MR-Linac is that the by being able to predict a future target location, the leaves of the multi-leaf collimator (MLC) will be able to conform to the target contour a its predicted future position. Thus, predicting future tumor position using MRI occurs at the same rate as imaging frequency during tracking. By being able to track the movement of a target tumor clearly using detailed MRI imaging allows for the delivery of a highly conformal radiation dose to the moving target.

In some embodiments, image acquisition device 320 may be an imaging device other than an MRI, such as an X-ray, a CT, a CBCT, a spiral CT, a PET, a SPECT, an optical tomography, a fluorescence imaging, ultrasound imaging, or radiotherapy portal imaging device, etc. As would be recognized by one of ordinary skill in the art, the above description of image acquisition device 320 concerns certain embodiments and is not intended to be limiting.

Radiotherapy device 330 may include the source of radiation 331, such as an X-ray source or a linear accelerator, and a multi-leaf collimator (MLC) 333. Radiotherapy device 330 may be mounted on a chassis 335. One or more chassis motors (not shown) may rotate chassis 335 around couch 310 when couch 310 is inserted into the treatment area. In an embodiment, chassis 335 may be continuously rotatable around couch 310, when couch 310 is inserted into the treatment area. Chassis 335 may also have an attached radiation detector (not shown), preferably located opposite to radiation source 331 and with the rotational axis of chassis 335 positioned between radiation source 331 and the detector. Further, device 330 may include control circuitry (not shown) used to control, for example, one or more of couch 310, image acquisition device 320, and radiotherapy device 330. The control circuitry of radiotherapy device 330 may be integrated within system 300 or remote from it.

During a radiotherapy treatment session, a patient may be positioned on couch 310. System 300 may then move couch 310 into the treatment area defined by magnetic coils 321, 325, 326, and chassis 335. Control circuitry may then control radiation source 331, MLC 333, and the chassis motor(s) to deliver radiation to the patient through the window between coils 325 and 326 according to a radiotherapy treatment plan.

Figure 4:
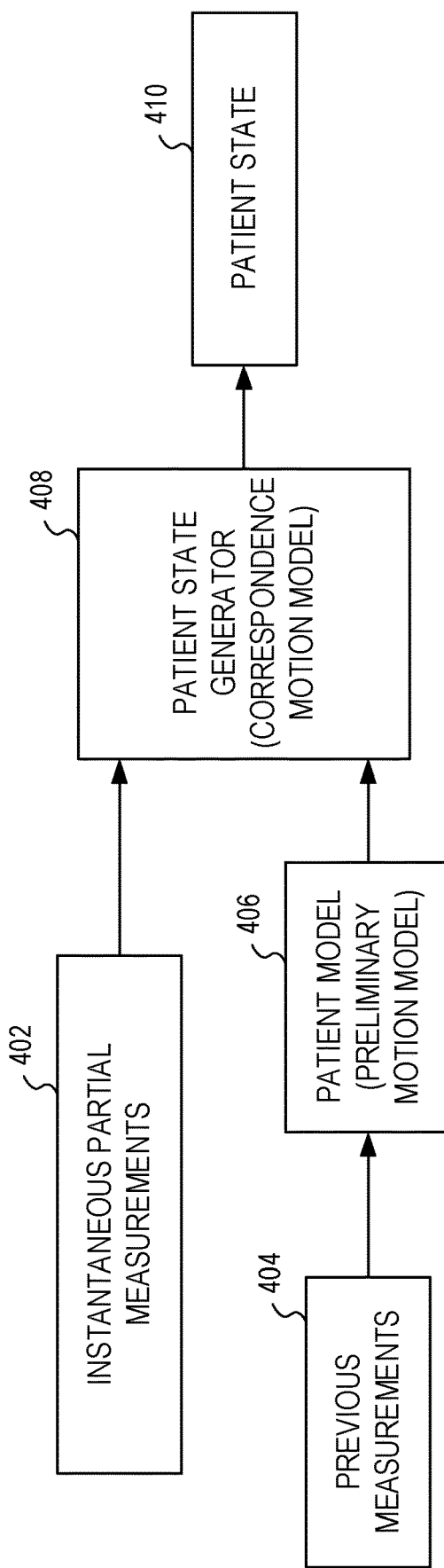
FIG. 4 illustrates an exemplary flow diagram for estimating a patient state using partial measurements and a preliminary patient model.

FIG. 4 illustrates an exemplary flow diagram for estimating a patient state. FIG. 4 includes a patient state generator 408 for estimating a patient state using a correspondence motion model. The patient state generator 408 uses an instantaneous partial measurement 402 and a preliminary motion model of a patient 406 to estimate a patient state, output at block 410. The preliminary motion model 406 is generated using previous measurements 404, including previous patient states corresponding to the previous measurements 404.

In practical radiotherapy applications, partial measurements (e.g., a 2D image or image slice) provide incomplete information about the patient state (e.g., a 3D image). For example, a 2D MRI slice is a single cut through a 3D representation of the patient, and an x-ray projection is an integration through voxels along ray-lines of a 3D representation. Using either image results in impartial information (e.g., a 2D image rather than a 3D representation of patient anatomy). The patient state generator 408 may use the partial information and the patient model 406 generated from past measurements and/or offline (pre-treatment) acquisitions to estimate the patient state 410.

The patient model generator 408 may include creation of a low dimensional patient state representation. In an example, prior measurements are first reconstructed into a 4D image. Examples may include a 4D CT acquired during a planning phase, which is used to generate a treatment plan; a 4D CBCT acquired immediately prior to each treatment session, with the patient in treatment position, generated for example by rotating a kV imager around the patient on a conventional linac; a 4D MR acquired prior to each treatment session on an MR-linac, or the like.

4D images may include a series of 3D images of a representative respiratory cycle. For example, for a 4D CBCT, a number of x-ray projections are acquired and sorted into a number of bins. Sorting may be done, for example, by detecting a diaphragm position in each projection directly in the images, or using a separate respiratory signal acquired simultaneously with the kV projections, and binning the projection according to the phase or amplitude of the signal. Each bin is then reconstructed separately with the kV projections assigned to that bin to form a 3D image per bin. Similar techniques may be used to generate a 4D MR image. A model may then be constructed using the 4D image as an interim step.

In an example, a reference phase of the 4D image is selected (for example, the one used for treatment planning), and a deformable image registration (DIR) is performed between the 3D image of each phase and that of the reference phase. The reference phase may include high-level treatment information (e.g. GTV, organs at risk, etc.). The output of the DIR process may include a displacement vector field (DVF) linking each phase to the reference phase.

Such a DVF-based motion model provides a mechanism for deforming the reference patient state (e.g., treatment information as defined on the 3D reference image) to the specific anatomy exhibited in each of the other phases of the representative respiratory cycle represented in the 4D dataset.

To interpolate and even extrapolate the preliminary motion model 406 to generate new DVFs, an unsupervised dimensionality reduction technique such as principal component analysis (PCA), independent component analysis (ICA), canonical correlation analysis (CCA), or the like may be used to identify one or more major degrees of freedom of the respiratory motion. In an example, 2 or 3 degrees of freedom may be sufficient to accurately estimate the patient state. In this example, additional degrees of freedom may be ignored or discarded (e.g., when they provide little useful information and are mostly noise). For example, a PCA of the DVF motion model may yield a low-dimensionality patient motion model that corresponds to a mean DVF and 2 or 3 DVF eigenmodes' (e.g., weighted inputs representing a degree of freedom). A DVF at any point in time in the motion cycle can be expressed as a weighted sum of the mean and the eigenmodes. For example, the mean DVF may be represented by $DVF_0$ and the eigenmodes may be $DVF_1$ and $DVF_2$, which are two full 3D vector fields, and then the DVF at any time during the cycle can be written as $DVF=DVF_0+a_1*DVF_1+a_2*DVF_2$ where $a_1$ and $a_2$ are scalar numbers and represent time variation. In this example, the motion model is reduced to identifying $a_1$ and $a_2$ instead of the entire DVF at a particular time. Once calculated, the DVF can then be used to warp the reference 3D image to obtain the current 3D image representing the patient state 310 (and can be extended to multiple patient images).

In some cases the interim step of reconstructing a 4D image may not be necessary, and the low dimensional state representation may be created directly from the measurements.

In an example, an advantage of using a pre-treatment 4D image is that the data is likely to be an excellent representation of the patient's respiratory degrees of freedom since it was acquired immediately prior to treatment. In some cases there may be advantages to using 4D images from a previous day, for instance, higher quality images may be possible (e.g., using an MRI if an MRI is not available during a treatment session, or a CT when only a CBCT is available prior to treatment), and more time can be spent generating and validating a patient model. In still another example, data from multiple patients may be used to generate a more robust model, such as to avoid over constraining the model.

Figure 5:
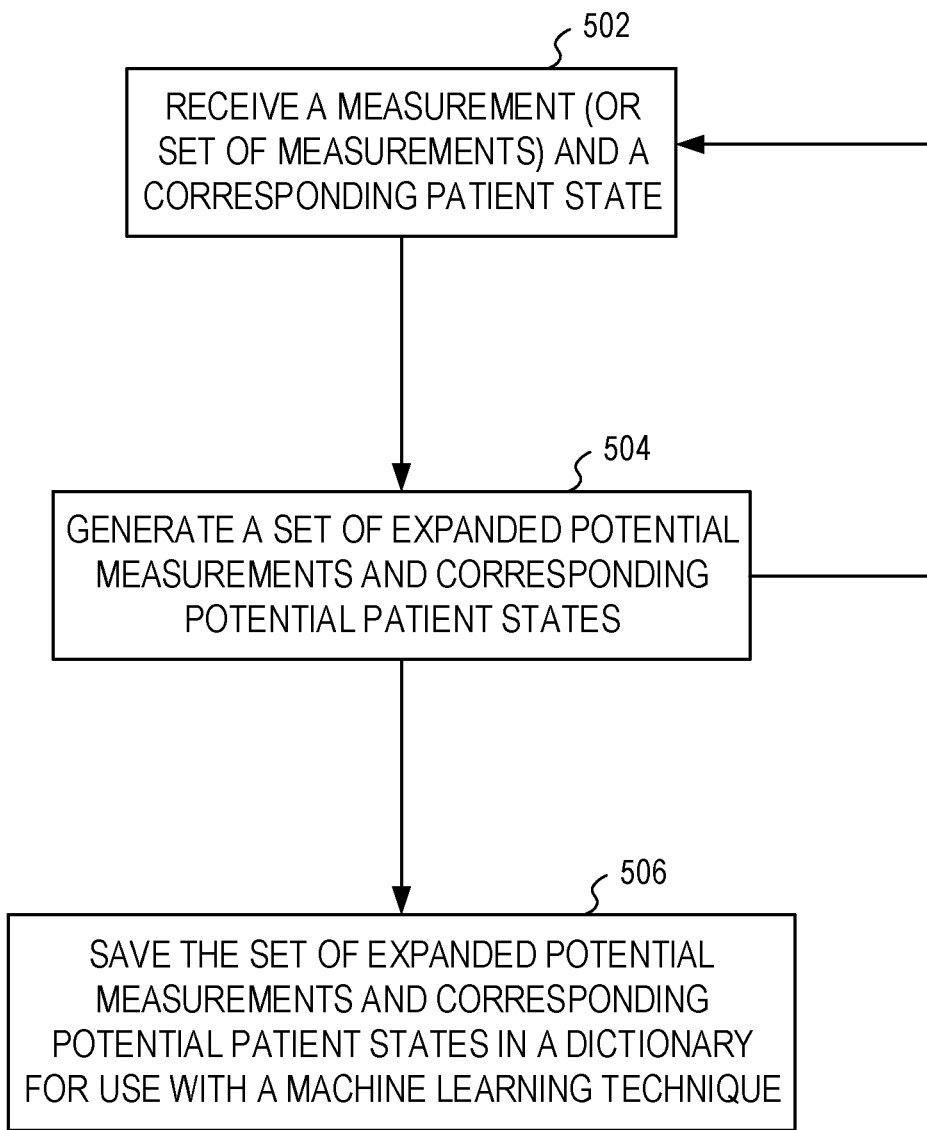
FIG. 5 illustrates an exemplary flowchart showing a patient state dictionary generation technique.

FIG. 5 illustrates an exemplary flowchart showing a patient state dictionary generation technique. Generation of a dictionary for use with a machine learning algorithm to output a patient state estimation may use coupled potential patient states and measurements.

The technique for generating the dictionary includes an operation 502 to receive a measurement or set of measurements, with a corresponding patient state or corresponding set of patient states. For example, a measurement may include a 2D image or other partial patient state information or data. The patient state may include a 3D or 4D representation of a patient, corresponding to the measurement. The dictionary thus may include labeled data for training or testing the machine learning algorithm. In an example, the received measurements may include digitally reconstructed radiograph (DRR) images for a CT-based patient model or 2D MRI slices for an MRI-based patient model.

In an example, generating the dictionary may include not using 2D images directly as measurements, but calculating a 2D DVF on the 2D images. For example, a PCA analysis of the 2D DVFs which results in a few parameters. In this example, the input is the 2D PCA of 2D DVF parameters. In another example, real-time 2D images are registered to a reference 2D image acquired during the same session (e.g., with same contrast). This allows for the use of a fast, highly-parallelizable, deformable image registration technique to generate 2D DVFs, such as the demon algorithm. The demon algorithm may be suitable for parallel implementation in GPU with real-time performance. In yet another example, a convolutional neural network (CNN) may be used to estimate the 2D optical flow between two images in real-time to generate 2D DVFs.

The technique includes an operation 504 to generate a set of expanded potential measurements and corresponding potential patient states. The potential measurements and potential patient states may be generated by taking an initial actual measurement (e.g., one received in operation 502) and a corresponding actual patient state and adding noise, perturbing, or otherwise extrapolating additional measurement-patient state pairs that potentially may occur for a given patient or patients. The operation 504 allows for generation of a set of labeled data from even a single actual measurement and patient state pair.

The technique includes an operation 506 to save the set of expanded potential measurements and corresponding potential patient states in a dictionary for use with a machine learning technique. In an example, the received measurement or set of measurements and the received corresponding patient state or set of patient states may also be saved in the dictionary for use with the machine learning technique. In an example, a measurement (actual or potential) may be used as input data to the machine learning technique, with the corresponding patient state (actual or potential) being the output from the machine learning technique, and the correspondence acting as the label for the data.

The expanded potential measurements may be generated in operation 504 using a low dimensional patient state representation (e.g., using PCA, ICA, CCA or the like). The low dimensional patient state representation may be used to generate possible patient states that could potentially occur during treatment. For example, a reasonable range of coefficients (e.g., $a_1$ and $a_2$ as described above in the DVF equation of the description of FIG. 3) may be subdivided into steps, such as equal steps, and the resulting patient state may calculated for each step. The results may form the dictionary of potential states corresponding to the potential measurement determined for each step. In an example, the coefficients are sampled randomly such that they are representative of most likely motions that occur in actual patients. For example, a Gaussian distribution, centered along the curve representing the average respiratory cycle, may be used to sample the coefficients. From the DVFs, the patient states (e.g. 3D patient images) are calculated by warping a reference image. In an example, the dictionary may be used to infer a 3D image from a 2D input, such as using regression analysis in a supervised machine learning algorithm.

In an example, to generate the set of expanded potential measurements and corresponding potential patient states, small rigid transformations may be applied to a 3D image for data augmentation to for potential patient translations. In an example, the dictionary of potential patient states may be generated from multiple patients rather than the particular patient under treatment, using acquired 3D images, biomechanical models, or the like. In another example, using the particular patient may be used for practical considerations to limit the data needed and ensure that the data is relevant to the patient being treated.

Using the PCA approach to generating the expanded potential measurements and potential patient states may include generating PCA coefficients. To generate realistic training patient states, coefficients may be randomly drawn according to a normal distribution, for example centered along an average trajectory (e.g., within the 4D dataset of a received patient state) with a standard distribution equivalent to a percentage of a dynamic range of each coefficient (e.g., 10%). Next, a PCA-to-DVF reconstruction is performed. A full DVF may be reconstructed using the randomly generated PCA coefficients (e.g., 2-3 coefficients representing degrees of freedom of the moving patient). The DVF is converted to a raw patient state volume by warping the reference volume using the full DVF. A partial measurement is created from the raw patient state volume. For a CT-based motion model, a 2D digitally reconstructed radiograph is computed from the raw patient state volume using, for example, a Siddon-Jacobs algorithm. For a MRI-based motion model, the 3D volume is resampled to extract a 2D MRI slice. Small rigid transformations are applied to the 3D volume for data augmentation to account for small differences in the patient position inter-fraction.

Together, the raw patient state volume output and the partial measurement are used together as a training sample to be saved to the dictionary (e.g., the input is the measurement and the output is the patient state). This workflow may be repeated for a number of training samples, such as 1,000s of samples, or an optimized number of training samples.

For each generated potential patient state, one or more potential patient measurements are simulated. These are measurements that may potentially have resulted in the corresponding state. For example, for a state represented by a 3D MRI image, a 2D slice from a particular orientation and position (e.g., sagittal) that is expected to be used during treatment can be extracted. For a 3D CBCT image, a kV x-ray projection can be simulated by ray-tracing through the 3D image and integrating voxels along the ray lines, such as by using the Siddon-Jacobs algorithm, for a particular gantry angle. More complex algorithms can be considered, such as using a Monte Carlo algorithm to simulate what a realistic 2D kV x-ray image potentially produces, including effects such as scattering and beam hardening. Imaging properties such as slice or gantry angle may be randomly sampled, or sampled uniformly, or fixed at known values. In some examples, a separate AI algorithm (e.g., Generative Adversarial Networks (GAN)) may be used to estimate measurements from patient states, particularly when the patient measurement cannot be easily calculated from the state (e.g., 2D MR slice measurements from 3D density patient state information). In some examples, the dimensionality of the dictionary may be further reduced by performing unsupervised dimensionality reduction (e.g., PCA, ICA, or CCA) on either the potential measurements or patient states. In other examples, a demon algorithm (with image registration to a reference image) or a CNN may be used to generate DVFs for the potential measurements.

Figure 6:
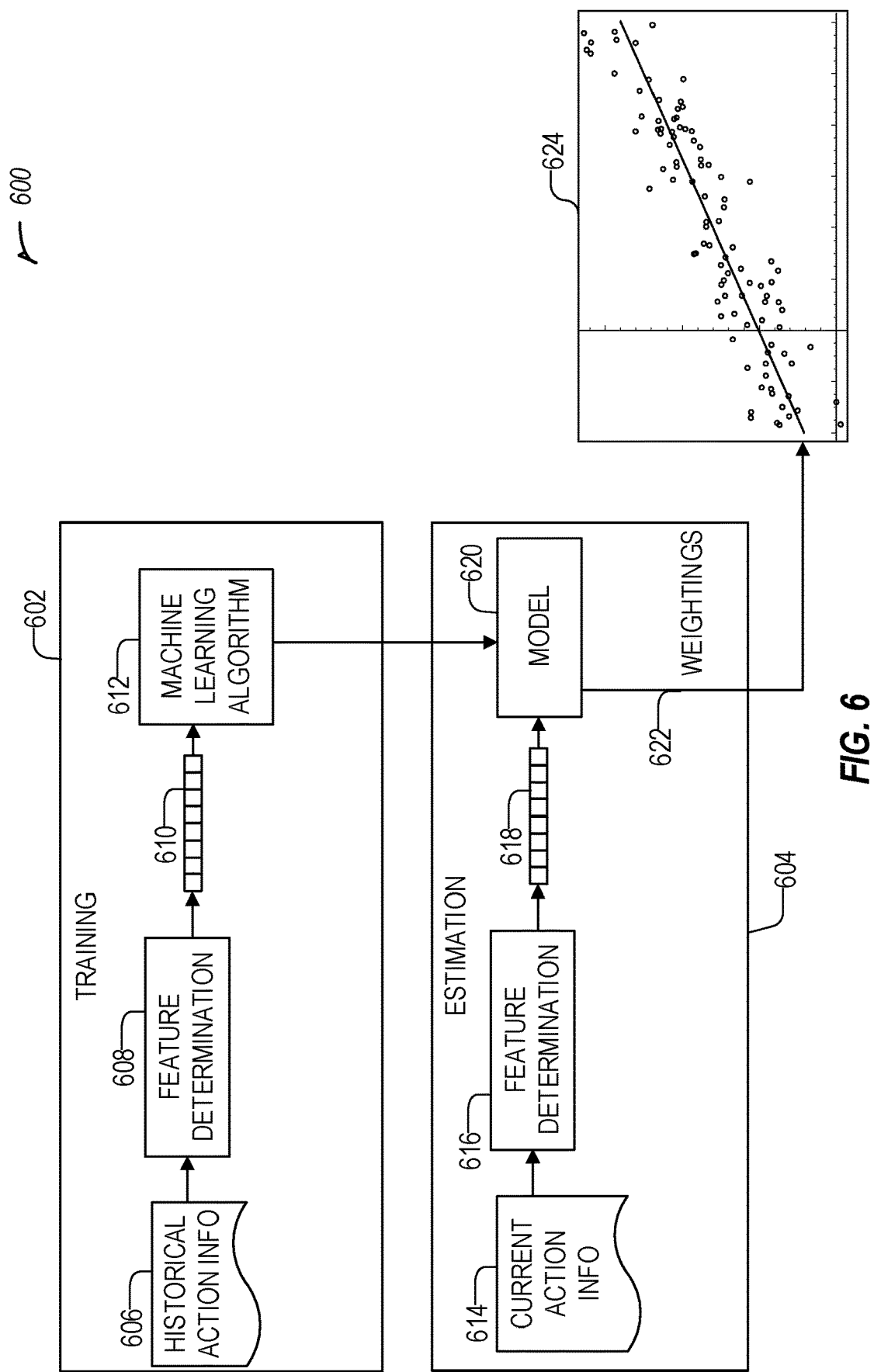
FIG. 6 illustrates an exemplary regression model machine learning engine for use in estimating a patient state.

FIG. 6 illustrates an exemplary regression model machine learning engine 600 for use in estimating a patient state. Machine learning engine 600 utilizes a training engine 602 and a estimation engine 604. Training engine 602 inputs historical transaction information 606 (e.g., patient measurements and corresponding patient states) into feature determination engine 608. The historical action information 606 may be labeled to indicate the correspondence between a measurement and a patient state.

Feature determination engine 608 determines one or more features 610 from this historical information 606. Stated generally, features 610 are a set of the information input and include information determined to be predictive of a particular outcome. The features 610 may be determined by hidden layers, in an example. The machine learning algorithm 612 produces a correspondence motion model 620 based upon the features 610 and the labels.

In the estimation engine 604, current action information 614 (e.g., a current patient measurement) may be input to the feature determination engine 616. Feature determination engine 616 may determine features of the current information 614 to estimate a corresponding patient state. In some examples, feature determination engine 616 and 608 are the same engine. Feature determination engine 616 produces feature vector 618, which is input into the model 620 to generate one or more criteria weightings 622. The training engine 602 may operate in an offline manner to train the model 620. The estimation engine 604, however, may be designed to operate in an online manner. It should be noted that the model 620 may be periodically updated via additional training or user feedback (e.g., additional, changed, or removed measurements or patient states).

The machine learning algorithm 612 may be selected from among many different potential supervised or unsupervised machine learning algorithms. Examples of supervised learning algorithms include artificial neural networks, Bayesian networks, instance-based learning, support vector machines, decision trees (e.g., Iterative Dichotomiser 3, C4.5, Classification and Regression Tree (CART), Chi-squared Automatic Interaction Detector (CHAID), and the like), random forests, linear classifiers, quadratic classifiers, k-nearest neighbor, linear regression, logistic regression, and hidden Markov models. Examples of unsupervised learning algorithms include expectation-maximization algorithms, vector quantization, and information bottleneck method. Unsupervised models may not have a training engine 602.

In an example, a regression model is used and the model 620 is a vector of coefficients corresponding to a learned importance for each of the features in the vector of features 610, 618. The regression model is illustrated in block 624, showing an example linear regression. The machine learning algorithm 612 is trained using a dictionary generated as described herein. The machine learning algorithm 612 trains on how patient measurements correspond to patient states. In an example, the machine learning algorithm 612 implements a regression problem (e.g., linear, polynomial, regression trees, kernel density estimation, support vector regression, random forests implementations, or the like). The resulting training parameters define the patient state generator as a correspondence motion model for the chosen machine learning algorithm.

In the conventional linac case, this training may be performed separately for every possible gantry angle (e.g., with a one degree increment), since x-ray acquisition orientation may be constrained to an orthogonal angle with respect to the treatment beam. In the MR-linac case, control may be given to a clinician on the 2D acquisition plane for position or orientation. Repeating cross-validation on training data with different choice of 2D planes can reveal which 2D planes yield best surrogate information for a given patient/tumor site.

In some cases a patient measurement may be used to update the model 620. In some cases a calculation may be performed to determine whether the patient measurement is consistent with the model 620, and pause the treatment if it is not (e.g., using a threshold on the variance for a KDE algorithm, or determining whether there is sufficient data in the dictionary in the neighborhood of the measurement). When the treatment is paused, a new model 620 may be generated, or the old model 620 may be reused if the measurement (e.g., motion) was an aberration.

In some applications the entire real-time patient image may not be necessary, and only features of it may be useful. For example the target centroid may be useful to make geometric corrections to multileaf collimators (MLCs), or to gate a beam on or off. In such cases, the single DVF vector connecting the center of the target in the reference image to the current target may be used rather than computing the entire 3D DVF and deforming the entire reference image at each time, which results in rendering the real-time process more efficient.

After the patient state generator has been successfully trained and the patient model 620 is aligned to the patient, the treatment beam is turned on and instantaneous partial measurements are acquired at a given frequency. For each received measurement, the process may include normalizing a 2D image of the received measurement to match the contrast of training images. The patient state generator may use the normalized measurement to infer model coefficients, and a DVF may be reconstructed using the model. The reconstructed DVF is used to warp the reference volume and treatment information to the current patient state, which may be output or saved.

In some cases, the model may not be well-aligned to the patient during treatment. This may occur if the patient moves between the 4D image and treatment, if a model from a previous day is used, or if data from other patients is used. The patient model (computed pre-treatment) may then be aligned to the actual patient position by rigid registration to new patient measurements with the patient in treatment position. During this time, a CBCT or MRI is acquired for coarse model-to-patient alignment. Fine alignment of patient model with multiple sample images (e.g., x-ray or 2D MRI slices) to account for couch shifts can be applied after CBCT or MRI acquisition.

Differences of contrast in synthetically generated training measurements versus actual 2D imaging acquisitions can hinder the generator's ability to infer 3D patient states. Some intensity normalization procedure may be used to correct for this issue. For example, local or global linear normalization methods may be used. Other examples may include the use of a Generative Adversarial Network (GAN) for mapping the intensities of real versus synthetic images.

Figure 7:
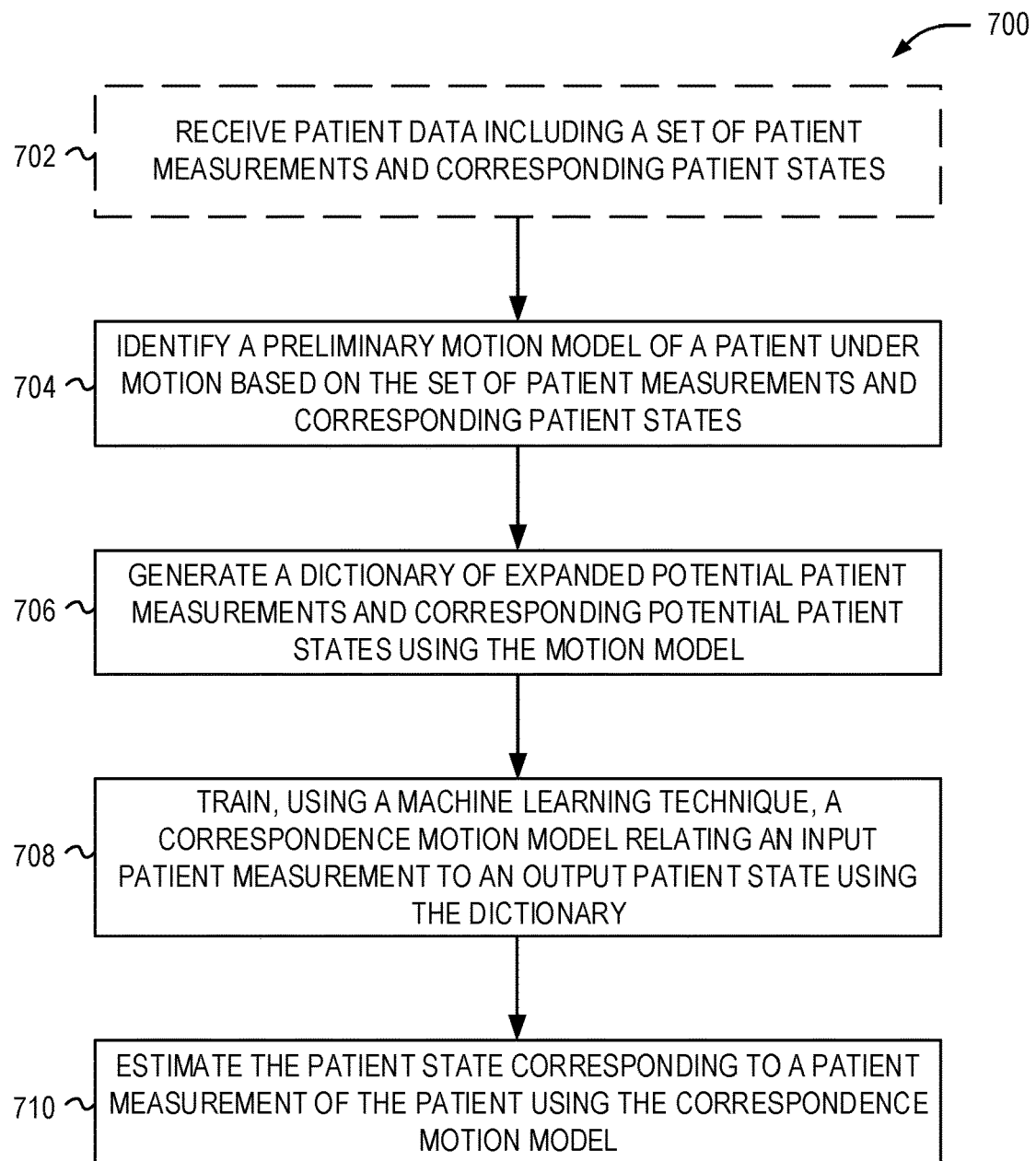
FIG. 7 illustrates a flowchart of exemplary operations for estimating a patient state.

FIG. 7 illustrates a flowchart 700 of exemplary operations for estimating a patient state. The flowchart 700 includes an optional operation 702 to receive, for example using a processor, patient data including a set of patient measurements and corresponding patient states. The corresponding patient states may include a 3D or a 4D patient image, such as a 3D CT, a 3D CBCT, a 3D MRI, a 3D PET, a 3D ultrasound, a 4D CT, a 4D CBCT, a 4D MRI, a 4D PET, or a 4D ultrasound image. The patient measurements may include a 2D MRI slice, MRI k-space data, a 1D MRI navigator, a 2D MRI projection, x-ray 2D projection data, PET data, a 2D ultrasound slice, or the like. In some cases, detectors may be arranged to obtain patient measurements from multiple views simultaneously, for example with stereoscopic kV imaging, or from multiple concurrent modalities, such as kV imaging combined with a surface camera. In one example, the patient data may be generated from a single patient. In another example, the patient data may be include data from a plurality of patients.

The flowchart 700 includes an operation 704 to identify a preliminary motion model of a patient under motion, for example based on the set of patient measurements and corresponding patient states. In an example, the preliminary motion model may be generated based on a 4D dataset acquired before a radiotherapy treatment. The preliminary motion model may be generated from a 4D MR or 4D CBCT acquired during treatment. A DVF may be calculated between each of the phases of this 4D image and a reference phase. A PCA analysis may be performed on these DVFs. The preliminary motion model may be a 3D DVF that is parametrized by 2-3 scalars, plus a reference 3D image. Potential 3D images may be generated that might occur during a treatment from the 2-3 scalars, by which a DVF may be calculated. This DVF may be used to deform the reference 3D image to calculate a new 3D image.

The flowchart 700 includes an operation 706 to generate a dictionary of expanded potential patient measurements and corresponding potential patient states using the motion model. The expanded potential patient measurements may include deformations of a 3D or a 4D patient image. In an example, the deformations include deformation vector fields (DVFs) calculated using a deformable registration algorithm. In an example, the expanded potential patient measurements include a 2D projection image. The expanded potential patient measurements may be generated using one or more of extracting a 2D slice from a 3D image, ray-tracing through a 3D image to generate a 2D projection image, simulating x-ray interactions with a 3D image using a Monte Carlo technique, using a collapsed cone convolution technique, using a superposition and convolution technique, using a generative adversarial network, using a convolutional neural network, using a recurrent neural network or the like. The dictionary may include possible 3D images that may occur during treatment by randomly sampling 2-3 scalars, generating to 3D DVFs from the scalars, and deforming the reference image, resulting in the corresponding potential patient states.

The expanded potential patient measurements may be generated by calculating a 2D DVF on a 2D input image. In an example, the 2D DVF may be calculated by performing a PCA analysis of the 2D input image. In another example, the 2D DVF may be calculated by registering the 2D input image to a reference 2D image (e.g., taken at the start or just before the start of radiation treatment), and using a deformable image registration technique. The 2D input image and the reference 2D image may have the same contrast to allow for registration. The deformable image registration technique may be a fast, highly-parallelizable technique, such as a demon algorithm (e.g., implemented in parallel on a GPU with real-time performance). In yet another example, the 2D DVF may be generated using a CNN to estimate a 2D optical flow between the 2D input image and a 2D reference image. The CNN may be run in real-time.

The corresponding potential patient states may be associated with a patient measurement that would have yielded respective patient states. For example, extracting a 2D slice through a 3D image, or a 2D projection through an image, at a particular location or angle. The raw 2D image may not be used in an example, as the measurement. Instead, a 2D DVF between the 2D image and a corresponding image form the reference 3D image may be used with a PCA analysis on the resulting 2D DVF. For example, the measurements may be processed versions of measurements, rather than directly measured patient data. The measurements may be PCA components of 2D DVFs, which may include the expanded potential patient measurements. The coupled expanded potential patient measurements (PCAs of 2D DVFs) and corresponding patient states (PCAs of 3D DVFs) may form the dictionary.

The flowchart 700 includes an operation 708 to train, using a machine learning technique, a correspondence motion model relating an input patient measurement to an output patient state using the dictionary. The correspondence motion model may include a deformation vector field (DVF) as a function of one or more parameters. In an example, the one or more parameters may be determined by reducing dimensionality of a preliminary DVF calculated between two or more phases of a 4D image and a reference phase. For example, reducing the dimensionality may include using a principal component analysis (PCA), an independent component analysis (ICA) or a canonical correlation analysis (CCA). In an example, the correspondence motion model may be generated using a random forest regression, a linear regression, a polynomial regression, a regression tree, a kernel density estimation, a support vector regression algorithm, a CNN, a RNN, or the like. The machine learning algortm may be used to relate the coupled entries in the dictionary. The algorithm may be used with a measurement input to provide a patient state. The measurement input may include a PCA component of a 2D DVF of a 2D image with a reference image, and the patient state may include a 3D DVF.

In an example, the preceding operations occur pre-treatment, while the following operations occur during treatment. The flowchart 700 includes an operation 710 to estimate the patient state corresponding to a patient measurement of the patient using the correspondence motion model. The patient state may be saved or output. For example, the patient state may be output for display on a user interface of a display device. In an example, estimating the patient state may include receiving the patient measurement as an input to the correspondence motion model, the input including a real-time stream of 2D images. The real-time stream of 2D images may include stereoscopic kV images (e.g., from a kV imager rotating around a patient with a conventional linac) or pairs of 2D MR slice images (e.g., from an MR-Linac). In an example, the stereoscopic kV images may include two x-ray images that are orthogonal or substantially orthogonal (e.g., within 10 degrees) which are acquired simultaneously or substantially simultaneously (e.g., within a few or a few hundred milliseconds). The kV imager may be fixed in a room or may be fixed to a gantry (e.g., including a linac). A pair of 2D MR slice images may be orthogonal to each other or parallel to each other. In another example, two kV imagers may be used, such as with each at 45 degrees to the treatment beam (and 90 degrees to each other). Both kV imagers in this example may be used simultaneously or they may be used in an alternating fashion.

In an example, images may be acquired from a kV imager or two kV imagers with simultaneously acquired internal ultrasound data. The ultrasound data may be used to reduce the kV dose by having, for example, less dose or pulse or to have a lower kV imaging frame rate. This secondary data may be included directly into the measurements to calculate patient state, or a separate correspondence model may be generated between the kV and secondary data streams and this separate model may be used to relate secondary data to patient state. For example, a correlation model may be built and continuously updated that relates kV PCA components to a parameter extracted from the secondary measurements stream, and as the secondary stream data is acquired, this correlation model may be used to determine the kV PCA components.

During treatment, a 2D image may be received. A 2D DVF may be calculated between the input 2D image and a reference 2D image. A PCA analysis may be performed on the DVF. The result is a real-time 'measurement' as used herein. The trained machine learning algorithm may take the measurement as an input and calculate PCA components of the 3D DVF from the input measurements. The PCA components are used to generate a 3D DVF, which is used to deform the 3D reference image with to 3D DVF to form the current real-time 3D patient image that represents the patient at a current time. The patient state may be the 3D image itself, the reference image plus the 3D DVF, or the like (in an example, one may be calculated from the other).

In an example, an operation may include outputting the patient state, such as outputting two or more MR-like 3D images showing tissue contrast, outputting non-imaging information, outputting CT-like 3D images, or the like.

Figure 8:
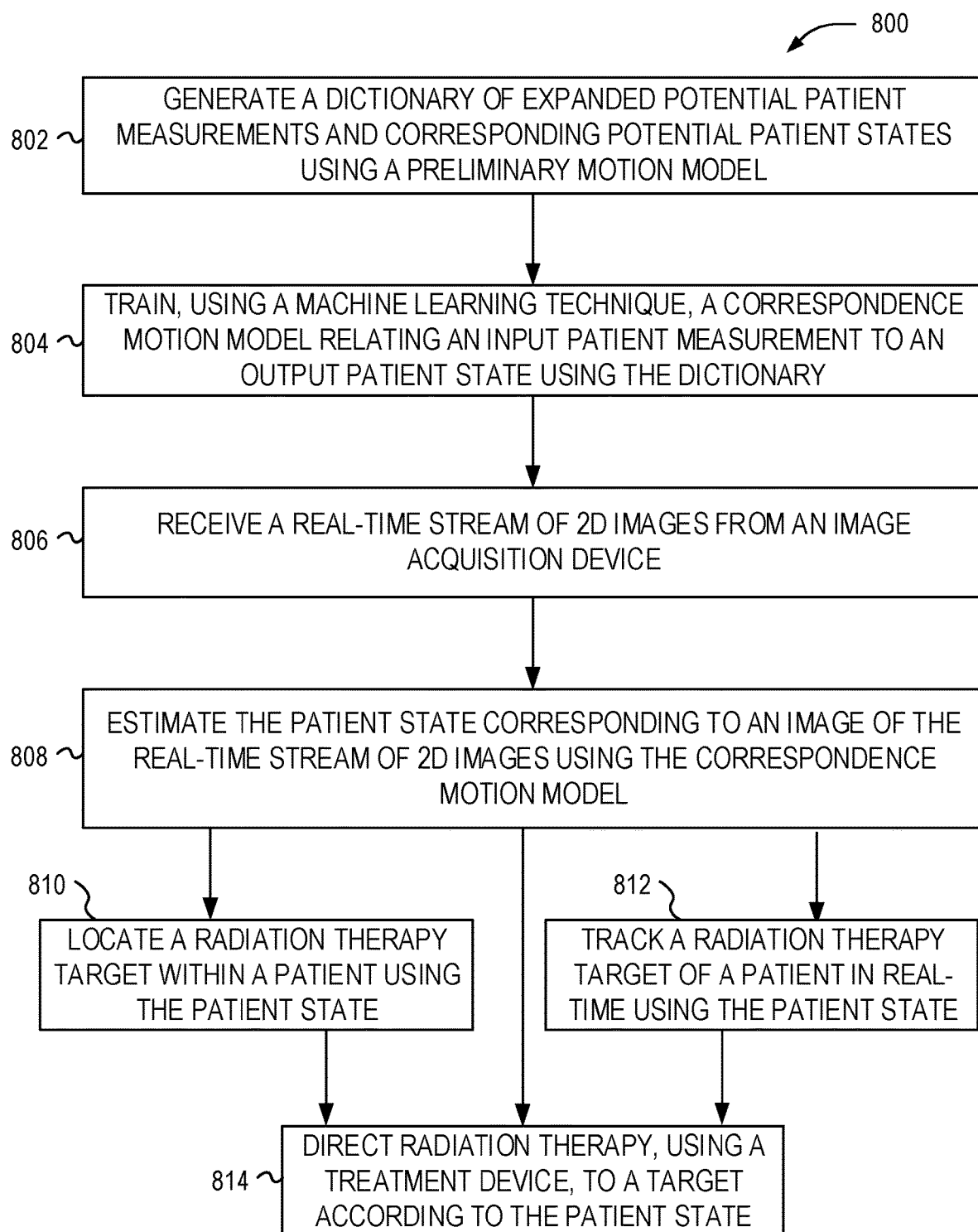
FIG. 8 illustrates a flowchart of exemplary operations for performing radiation therapy techniques.

FIG. 8 illustrates a flowchart of exemplary operations for performing radiation therapy techniques.

The flowchart 800 includes an operation 802 to generate a dictionary of expanded potential patient measurements and corresponding potential patient states using a motion model (e.g., as described above with respect to operation 706). The expanded potential patient measurements may be generated by calculating a 2D DVF on a 2D input image. In an example, the 2D DVF may be calculated by performing a PCA analysis of the 2D input image. In another example, the 2D DVF may be calculated by registering the 2D input image to a reference 2D image (e.g., taken at the start or just before the start of radiation treatment), and using a deformable image registration technique. The 2D input image and the reference 2D image may have the same contrast to allow for registration. The deformable image registration technique may be a fast, highly-parallelizable technique, such as a demon algorithm (e.g., implemented in parallel on a GPU with real-time performance). In yet another example, the 2D DVF may be generated using a CNN to estimate a 2D optical flow between the 2D input image and a 2D reference image. The CNN may be run in real-time.

In an example, the expanded potential patient measurements may be generated from a 4D image, the 4D image including a 4D CT, a 4D CBCT, a 4D MRI, a 4D PET, a 4D ultrasound image, or the like. In an example, the expanded potential patient measurements include a 2D projection image and are generated by using at least one of: extracting a 2D slice from a 3D image, ray-tracing through a 3D image to generate a 2D projection image, simulating x-ray interactions with a 3D image using a Monte Carlo technique, using a collapsed cone convolution technique, using a superposition and convolution technique, using a generative adversarial network, a convolutional neural network, a recurrent neural network, or the like.

The flowchart 800 includes an operation 804 to train, using a machine learning technique, a correspondence motion model relating an input patient measurement to an output patient state using the dictionary (e.g., as described above with respect to operation 708). The correspondence motion model may include a deformation vector field (DVF) as a function of one or more parameters, the one or more parameters determined by reducing dimensionality of a preliminary DVF calculated between two or more phases of a 4D image and a reference phase. The correspondence motion model may be generated using a random forest regression, a linear regression, a polynomial regression, a regression tree, a kernel density estimation, a support vector regression algorithm, a convolutional neural network, a recurrent neural network, or the like.

The flowchart 800 includes an operation 806 to receive a real-time stream of 2D images from an image acquisition device (e.g., a kV x-ray, a MR device, a CT device, or other image acquisition device). The real-time stream of 2D images may include stereoscopic kV images (e.g., from a kV imager rotating around a patient with a conventional linac) or pairs of 2D MR slice images (e.g., from an MR-Linac). In another example, the real-time stream of 2D images may include k-space data, low resolution 3D MR images, 1D navigators, or other MR information.

In an example, the stereoscopic kV images may include two x-ray images that are orthogonal or substantially orthogonal (e.g., within 10 degrees) which are acquired simultaneously or substantially simultaneously (e.g., within a few or a few hundred milliseconds). The kV imager may be fixed in a room or may be fixed to a gantry (e.g., including a linac). A pair of 2D MR slice images may be orthogonal to each other or parallel to each other.

The flowchart 800 includes an operation 808 to estimate the patient state corresponding to an image of the real-time stream of 2D images using the correspondence motion model. The patient state may be output, for example as an image (e.g., a 3D MR or CT), as non-image information, or both. The patient state may include information (e.g., an image or text) describing patient anatomy, such as a tumor or organ of interest, or may be used to establish a target, such as a radiation therapy target (e.g., on a portion of a tumor).

The flowchart 800 includes an operation 810 to locate a radiation therapy target within a patient using the patient state.

The flowchart 800 includes an operation 812 to track a radiation therapy target of a patient in real-time using the patient state. For example, successive images from the real-time stream of 2D images may be used to output corresponding patient states, with a target tracked from one patient state to the next.

The flowchart 800 includes an operation 814 to direct radiation therapy, using a treatment device (e.g., a stand-alone treatment device, a device coupled to an image acquisition device (e.g., an MR-linac), or the like), to a target according to the patient state. For example, the target may be located in operation 810 or tracked in operation 812, and radiation therapy may be applied according to the location or tracking. In an example, location or tracking information may be displayed on a display device, such as with a user interface presented on the display device.

ADDITIONAL NOTES

The above detailed description includes references to the accompanying drawings, which form a part of the detailed description. The drawings show, by way of illustration but not by way of limitation, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the invention or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," etc., are used merely as labels, and are not intended to impose numerical requirements on their objects.

The present invention also relates to a computing system adapted, configured, or operated for performing the operations herein. This system may be specially constructed for the required purposes, or it may comprise a general purpose computer selectively activated or reconfigured by a computer program (e.g., instructions, code, etc.) stored in the computer. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In view of the above, it will be seen that the several objects of the invention are achieved and other advantageous results attained. Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the invention without departing from its scope. While the dimensions, types of materials and example parameters, functions, and implementations described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

Each of these non-limiting examples may stand on its own, or may be combined in various permutations or combinations with one or more of the other examples.

Example 1 is a method for estimating a real-time patient state during a radiotherapy treatment, the method comprising: receiving, using a processor, patient data including a set of constructed patient measurements; identifying a preliminary motion model of a patient under motion based on the set of constructed patient measurements; generating a dictionary of expanded potential patient measurements and corresponding potential patient states using the preliminary motion model; training, using a machine learning technique, a correspondence motion model relating an input patient measurement to an output patient state using the dictionary; and estimating, using the processor, the patient state corresponding to a patient measurement of the patient using the correspondence motion model.

In Example 2, the subject matter of Example 1 includes, wherein the corresponding patient states include a 3D patient image.

In Example 3, the subject matter of Example 2 includes, wherein the corresponding potential patient states include deformations of the 3D patient image.

In Example 4, the subject matter of Example 3 includes, wherein the deformations include deformation vector fields (DVFs) calculated using a deformable registration algorithm.

In Example 5, the subject matter of Examples 1-4 includes, wherein the patient measurements include a 2D MRI slice, MRI k-space data, a 1D MRI navigator, a 2D MRI projection, x-ray 2D projection data, PET data, or a 2D ultrasound slice.

In Example 6, the subject matter of Examples 1-5 includes, wherein the patient data includes a 4D image.

In Example 7, the subject matter of Example 6 includes, wherein the 4D image is a 4D CT, a 4D CBCT, a 4D MRI, a 4D PET, or a 4D ultrasound image.

In Example 8, the subject matter of Examples 1-7 includes, wherein the correspondence motion model includes a deformation vector field (DVF) as a function of one or more parameters, the one or more parameters determined by reducing dimensionality of a preliminary DVF calculated between two or more phases of a 4D image and a reference phase.

In Example 9, the subject matter of Examples 1-8 includes, wherein the expanded potential patient measurements include a 2D projection image and are generated by using at least one of: extracting a 2D slice from a 3D image, ray-tracing through a 3D image to generate a 2D projection image, simulating x-ray interactions with a 3D image using a Monte Carlo technique, using a collapsed cone convolution technique, using a superposition and convolution technique, using a generative adversarial network, a convolutional neural network, or a recurrent neural network.

In Example 10, the subject matter of Examples 1-9 includes, wherein the correspondence motion model is generated using a random forest regression, a linear regression, a polynomial regression, a regression tree, a kernel density estimation, a support vector regression algorithm, a convolutional neural network, or a recurrent neural network.

In Example 11, the subject matter of Examples 1-10 includes, wherein estimating the patient state corresponding to the patient measurement includes receiving the patient measurement as an input to the correspondence motion model, the input including a real-time stream of 2D images.

In Example 12, the subject matter of Example 11 includes, wherein the real-time stream of 2D images includes stereoscopic kV images or pairs of 2D MR slice images.

In Example 13, the subject matter of Examples 1-12 includes, outputting the patient state as two or more MR-like 3D images showing tissue contrast.

In Example 14, the subject matter of Examples 1-13 includes, wherein the patient state includes non-imaging information.

In Example 15, the subject matter of Examples 1-14 includes, generating the preliminary motion model based on a 4D dataset acquired before the radiotherapy treatment.

In Example 16, the subject matter of Examples 1-15 includes, generating the constructed patient measurements by calculating a 2D deformation vector field (DVF) on a 2D input image.

In Example 17, the subject matter of Examples 1-16 includes, wherein generating the constructed patient measurements includes performing a principal component analysis (PCA) analysis of the 2D 2D input image.

In Example 18, the subject matter of Examples 1-17 includes, wherein generating the constructed patient measurements includes registering the 2D input image to a reference 2D image, and using a deformable image registration technique to calculate the 2D DVF.

In Example 19, the subject matter of Examples 1-18 includes, wherein generating the constructed patient measurements includes using a convolutional neural network (CNN) to estimate a 2D optical flow between the 2D input image and a 2D reference image to calculate the 2D DVF.

Example 20 is a system for estimating a patient state during a radiotherapy treatment, the system comprising: a processor coupled to memory, the memory including instructions, which when executed by the processor, cause the processor to perform operations to: receive patient data including a set of constructed patient measurements; identify a preliminary motion model of a patient under motion based on the set of constructed patient measurements; generate a dictionary of expanded potential patient measurements and corresponding potential patient states using the preliminary motion model; train, using a machine learning technique, a correspondence motion model relating an input patient measurement to an output patient state using the dictionary; and estimate the patient state corresponding to a patient measurement of the patient using the correspondence motion model.

Example 21 is a method for estimating a real-time patient state during a radiotherapy treatment using a magnetic resonance linear accelerator (MR-Linac), the method comprising: generating a dictionary of expanded potential patient measurements and corresponding potential patient states using a preliminary motion model; training, using a machine learning technique, a correspondence motion model relating an input patient measurement to an output patient state using the dictionary; receiving a real-time stream of 2D MR images from an image acquisition device; estimating, using the processor, the patient state corresponding to an image of the real-time stream of 2D MR images using the correspondence motion model; and directing radiation therapy, using a treatment device coupled to the image acquisition device, to a target according to the patient state.

In Example 22, the subject matter of Example 21 includes, wherein the expanded potential patient measurements include deformations of a 3D patient image, and wherein the deformations include deformation vector fields (DVFs) calculated using a deformable registration algorithm.

In Example 23, the subject matter of Examples 21-22 includes, wherein the expanded potential patient measurements are generated from a 4D image, the 4D image including a 4D CT, a 4D CBCT, a 4D MRI, a 4D PET, or a 4D ultrasound image.

In Example 24, the subject matter of Examples 21-23 includes, wherein the correspondence motion model includes a deformation vector field (DVF) as a function of one or more parameters, the one or more parameters determined by reducing dimensionality of a preliminary DVF calculated between two or more phases of a 4D image and a reference phase.

In Example 25, the subject matter of Examples 21-24 includes, wherein the expanded potential patient measurements include a 2D projection image and are generated by using at least one of: extracting a 2D slice from a 3D image, ray-tracing through a 3D image to generate a 2D projection image, simulating x-ray interactions with a 3D image using a Monte Carlo technique, using a collapsed cone convolution technique, using a superposition and convolution technique, using a generative adversarial network, a convolutional neural network, or a recurrent neural network.

In Example 26, the subject matter of Examples 21-25 includes, wherein the correspondence motion model is generated using a random forest regression, a linear regression, a polynomial regression, a regression tree, a kernel density estimation, a support vector regression algorithm, a convolutional neural network, or a recurrent neural network.

In Example 27, the subject matter of Examples 21-26 includes, outputting the patient state as two or more MR-like 3D images showing tissue contrast.

In Example 28, the subject matter of Examples 21-27 includes, generating the expanded potential patient measurements by calculating a 2D deformation vector field (DVF) on a 2D input image.

In Example 29, the subject matter of Examples 21-28 includes, wherein generating the expanded potential patient measurements includes performing a principal component analysis (PCA) analysis of the 2D input image.

In Example 30, the subject matter of Examples 21-29 includes, wherein generating the expanded potential patient measurements includes registering the 2D input image to a reference 2D image, and using a deformable image registration technique to calculate the 2D DVF.

In Example 31, the subject matter of Examples 21-30 includes, wherein generating the expanded potential patient measurements includes using a convolutional neural network (CNN) to estimate a 2D optical flow between the 2D input image and a 2D reference image to calculate the 2D DVF.

Example 32 is a method for generating real-time target localization data, the method comprising: generating a dictionary of expanded potential patient measurements and corresponding potential patient states using a preliminary motion model; training, using a machine learning technique, a correspondence motion model relating an input patient measurement to an output patient state using the dictionary; receiving a real-time stream of 2D images from an image acquisition device; estimating, using the processor, the patient state corresponding to an image of the real-time stream of 2D images using the correspondence motion model; locating a radiation therapy target within a patient using the patient state; and outputting the location of the radiation therapy target on a display device.

In Example 33, the subject matter of Example 32 includes, wherein the real-time stream of 2D images includes stereoscopic kV images or pairs of 2D MR slice images.

In Example 34, the subject matter of Examples 32-33 includes, wherein the expanded potential patient measurements include deformations of a 3D patient image, and wherein the deformations include deformation vector fields (DVFs) calculated using a deformable registration algorithm.

In Example 35, the subject matter of Examples 32-34 includes, wherein the expanded potential patient measurements are generated from a 4D image, the 4D image including a 4D CT, a 4D CBCT, a 4D MRI, a 4D PET, or a 4D ultrasound image.

In Example 36, the subject matter of Examples 32-35 includes, wherein the correspondence motion model includes a deformation vector field (DVF) as a function of one or more parameters, the one or more parameters determined by reducing dimensionality of a preliminary DVF calculated between two or more phases of a 4D image and a reference phase.

In Example 37, the subject matter of Examples 32-36 includes, wherein the expanded potential patient measurements include a 2D projection image and are generated by using at least one of: extracting a 2D slice from a 3D image, ray-tracing through a 3D image to generate a 2D projection image, simulating x-ray interactions with a 3D image using a Monte Carlo technique, using a collapsed cone convolution technique, using a superposition and convolution technique, using a generative adversarial network, a convolutional neural network, or a recurrent neural network.

In Example 38, the subject matter of Examples 32-37 includes, wherein the correspondence motion model is generated using a random forest regression, a linear regression, a polynomial regression, a regression tree, a kernel density estimation, a support vector regression algorithm, a convolutional neural network, or a recurrent neural network.

In Example 39, the subject matter of Examples 32-38 includes, outputting the patient state as two or more MR-like 3D images showing tissue contrast.

In Example 40, the subject matter of Examples 32-39 includes, generating the expanded potential patient measurements by calculating a 2D deformation vector field (DVF) on a 2D input image.

In Example 41, the subject matter of Examples 32-40 includes, wherein generating the expanded potential patient measurements includes performing a principal component analysis (PCA) analysis of the 2D input image.

In Example 42, the subject matter of Examples 32-41 includes, wherein generating the expanded potential patient measurements includes registering the 2D input image to a reference 2D image, and using a deformable image registration technique to calculate the 2D DVF.

In Example 43, the subject matter of Examples 32-42 includes, wherein generating the expanded potential patient measurements includes using a convolutional neural network (CNN) to estimate a 2D optical flow between the 2D input image and a 2D reference image to calculate the 2D DVF.

Example 44 is a method for real-time tracking of a target, the method comprising: generating a dictionary of expanded potential patient measurements and corresponding potential patient states using a preliminary motion model; training, using a machine learning technique, a correspondence motion model relating an input patient measurement to an output patient state using the dictionary; receiving a real-time stream of 2D images from an image acquisition device; estimating, using the processor, patient states corresponding to images in the real-time stream of 2D images using the correspondence motion model; tracking a radiation therapy target of a patient in real-time using the patient states; and outputting tracking information for the radiation therapy target for display on a display device.

In Example 45, the subject matter of Example 44 includes, wherein the real-time stream of 2D images includes stereoscopic kV images or pairs of 2D MR slice images.

In Example 46, the subject matter of Examples 44-45 includes, wherein the expanded potential patient measurements include deformations of a 3D patient image, and wherein the deformations include deformation vector fields (DVFs) calculated using a deformable registration algorithm.

In Example 47, the subject matter of Examples 44-46 includes, wherein the expanded potential patient measurements are generated from a 4D image, the 4D image including a 4D CT, a 4D CBCT, a 4D MRI, a 4D PET, or a 4D ultrasound image.

In Example 48, the subject matter of Examples 44-47 includes, wherein the correspondence motion model includes a deformation vector field (DVF) as a function of one or more parameters, the one or more parameters determined by reducing dimensionality of a preliminary DVF calculated between two or more phases of a 4D image and a reference phase.

In Example 49, the subject matter of Examples 44-48 includes, wherein the expanded potential patient measurements include a 2D projection image and are generated by using at least one of: extracting a 2D slice from a 3D image, ray-tracing through a 3D image to generate a 2D projection image, simulating x-ray interactions with a 3D image using a Monte Carlo technique, using a collapsed cone convolution technique, using a superposition and convolution technique, using a generative adversarial network, a convolutional neural network, or a recurrent neural network.

In Example 50, the subject matter of Examples 44-49 includes, wherein the correspondence motion model is generated using a random forest regression, a linear regression, a polynomial regression, a regression tree, a kernel density estimation, a support vector regression algorithm, a convolutional neural network, or a recurrent neural network.

In Example 51, the subject matter of Examples 44-50 includes, outputting the patient state as two or more MR-like 3D images showing tissue contrast.

In Example 52, the subject matter of Examples 44-51 includes, generating the expanded potential patient measurements by calculating a 2D deformation vector field (DVF) on a 2D input image.

In Example 53, the subject matter of Examples 44-52 includes, wherein generating the expanded potential patient measurements includes performing a principal component analysis (PCA) analysis of the 2D input image.

In Example 54, the subject matter of Examples 44-53 includes, wherein generating the expanded potential patient measurements includes registering the 2D input image to a reference 2D image, and using a deformable image registration technique to calculate the 2D DVF.

In Example 55, the subject matter of Examples 44-54 includes, wherein generating the expanded potential patient measurements includes using a convolutional neural network (CNN) to estimate a 2D optical flow between the 2D input image and a 2D reference image to calculate the 2D DVF.

Example 56 is at least one machine-readable medium including instructions that, when executed by processing circuitry, cause the processing circuitry to perform operations to implement of any of Examples 1-55.

Example 57 is an apparatus comprising means to implement of any of Examples 1-55.

Example 58 is a system to implement of any of Examples 1-55.

Example 59 is a method to implement of any of Examples 1-55.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A method for estimating a real-time patient state during a radiotherapy treatment using a magnetic resonance linear accelerator (MR-Linac), the method comprising:
    generating a dictionary of simulated expanded potential patient measurements and corresponding simulated potential patient states using a preliminary motion model and based on an initial actual measurement and a corresponding initial actual patient state;
    training, using a machine learning technique, a correspondence motion model relating an input patient measurement to an output patient state using the dictionary;
    receiving a real-time stream of images from an image acquisition device;
    estimating, using the processor, the patient state corresponding to an image of the real-time stream of images using the correspondence motion model; and
    directing radiation therapy, using a treatment device coupled to the image acquisition device, to a target according to the patient state.

2. The method of claim 1, wherein the simulated expanded potential patient measurements include deformations of a 3D patient image, and wherein the deformations include deformation vector fields (DVFs) calculated using a deformable registration algorithm.

3. The method of claim 1, wherein the simulated expanded potential patient measurements are generated from a 4D image, the 4D image including a 4D CT, a 4D CBCT, a 4D MM, a 4D PET, or a 4D ultrasound image.

4. The method of claim 1, wherein the correspondence motion model includes a deformation vector field (DVF) as a function of one or more parameters, the one or more parameters determined by reducing dimensionality of a preliminary DVF calculated between two or more phases of a 4D image and a reference phase.

5. The method of claim 1, wherein the simulated expanded potential patient measurements include a 2D projection image and are generated by using at least one of:
    extracting a 2D slice from a 3D image, ray-tracing through a 3D image to generate a 2D projection image, simulating x-ray interactions with a 3D image using a Monte Carlo technique, using a collapsed cone convolution technique, using a superposition and convolution technique, using a generative adversarial network, a convolutional neural network, or a recurrent neural network.

6. The method of claim 1, wherein the correspondence motion model is generated using a random forest regression, a linear regression, a polynomial regression, a regression tree, a kernel density estimation, a support vector regression algorithm, a convolutional neural network, or a recurrent neural network.

7. The method of claim 1, further comprising outputting the patient state as two or more MR-like 3D images showing tissue contrast.

8. The method of claim 1, further comprising generating the simulated expanded potential patient measurements by calculating a 2D deformation vector field (DVF) on a 2D input image.

9. The method of claim 8, wherein generating the simulated expanded potential patient measurements includes performing a principal component analysis (PCA) analysis of the 2D input image.

10. The method of claim 9, wherein generating the simulated expanded potential patient measurements includes registering the 2D input image to a reference 2D image, and using a deformable image registration technique to calculate the 2D DVF, and using a convolutional neural network (CNN) to estimate a 2D optical flow between the 2D input image and a 2D reference image to calculate the 2D DVF.

11. The method of claim 1, wherein the real-time stream of images include 2D MR images, low resolution 3D MR images, or 1D navigators.

12. A method for real-time tracking of a target, during a radiotherapy treatment using a magnetic resonance linear accelerator (MR-Linac), the method comprising:
    generating a dictionary of simulated expanded potential patient measurements and corresponding simulated potential patient states using a preliminary motion model and based on an initial actual measurement and a corresponding initial actual patient state;
    training, using a machine learning technique, a correspondence motion model relating an input patient measurement to an output patient state using the dictionary;
    receiving a real-time stream of images from an image acquisition device;
    estimating, using the processor, patient states corresponding to images in the real-time stream of images using the correspondence motion model;
    tracking a radiation therapy target of a patient in real-time using the patient states; and
    outputting tracking information for the radiation therapy target for display on a display device.

13. The method of claim 12, wherein the simulated expanded potential patient measurements include deformations of a 3D patient image, and wherein the deformations include deformation vector fields (DVFs) calculated using a deformable registration algorithm.

14. The method of claim 12, wherein the simulated expanded potential patient measurements are generated from a 4D image, the 4D image including a 4D CT, a 4D CBCT, a 4D MM, a 4D PET, or a 4D ultrasound image.

15. The method of claim 12, wherein the correspondence motion model includes a deformation vector field (DVF) as a function of one or more parameters, the one or more parameters determined by reducing dimensionality of a preliminary DVF calculated between two or more phases of a 4D image and a reference phase.

16. The method of claim 12, wherein the simulated expanded potential patient measurements include a 2D projection image and are generated by using at least one of:
extracting a 2D slice from a 3D image, ray-tracing through a 3D image to generate a 2D projection image, simulating x-ray interactions with a 3D image using a Monte Carlo technique, using a collapsed cone convolution technique, using a superposition and convolution technique, using a generative adversarial network, a convolutional neural network, or a recurrent neural network.

17. The method of claim 12, wherein the correspondence motion model is generated using a random forest regression, a linear regression, a polynomial regression, a regression tree, a kernel density estimation, a support vector regression algorithm, a convolutional neural network, or a recurrent neural network.

18. The method of claim 12, further comprising outputting the patient state as two or more MR-like 3D images showing tissue contrast.

19. The method of claim 12, further comprising generating the simulated expanded potential patient measurements by calculating a 2D deformation vector field (DVF) on a 2D input image, and performing a principal component analysis (PCA) analysis of the 2D input image.

20. The method of claim 12, wherein the real-time stream of images include 2D MR images, low resolution 3D MR images, or 1D navigators.

\* \* \* \* \*